(12) United States Patent
Chen et al.

(10) Patent No.: US 10,306,895 B2
(45) Date of Patent: Jun. 4, 2019

(54) PLANT DEFENSE SIGNALING PEPTIDES AND APPLICATIONS THEREOF

(71) Applicant: Academia Sinica, Taipei (TW)

(72) Inventors: Yet-Ran Chen, Taipei (TW); Ying-Lan Chen, New Taipei (TW); Mei-Chun Tseng, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/521,927

(22) PCT Filed: Oct. 27, 2015

(86) PCT No.: PCT/US2015/057621
§ 371 (c)(1),
(2) Date: Apr. 26, 2017

(87) PCT Pub. No.: WO2016/069623
PCT Pub. Date: May 6, 2016

(65) Prior Publication Data
US 2017/0332645 A1  Nov. 23, 2017

Related U.S. Application Data

(60) Provisional application No. 62/068,987, filed on Oct. 27, 2014.

(51) Int. Cl.
| | |
|---|---|
| *C07K 14/00* | (2006.01) |
| *A61K 36/00* | (2006.01) |
| *A61K 36/06* | (2006.01) |
| *A61K 38/00* | (2006.01) |
| *A61K 38/01* | (2006.01) |
| *A61K 38/03* | (2006.01) |
| *A61K 38/04* | (2006.01) |
| *A61K 38/08* | (2006.01) |
| *A61K 38/10* | (2006.01) |
| *A61K 38/16* | (2006.01) |
| *A01N 65/38* | (2009.01) |
| *C07K 14/415* | (2006.01) |
| *C12N 15/82* | (2006.01) |

(52) U.S. Cl.
CPC ............ *A01N 65/38* (2013.01); *C07K 14/415* (2013.01); *C12N 15/8271* (2013.01); *C12N 15/8279* (2013.01); *A61K 38/00* (2013.01)

(58) Field of Classification Search
CPC .. C07K 14/415; C07K 14/4723; C07K 14/00; A61K 36/00; A61K 36/06; A61K 38/00; A61K 38/011; A61K 38/03; A61K 38/04; A61K 38/08; A61K 38/10; A61K 38/16
USPC ......... 530/300, 324, 325, 326, 327; 514/1.1, 514/2.3, 3.3, 21.2, 21.3, 21.4, 21.5, 21.6
See application file for complete search history.

(56) References Cited

U.S. PATENT DOCUMENTS

2013/0061352 A1  3/2013  Ryan et al.

FOREIGN PATENT DOCUMENTS

| WO | WO 1992/020800 A1 | 11/1992 |
| WO | WO 2013/039857 A1 | 3/2013 |

OTHER PUBLICATIONS

Chen et al., Quantitative peptidomics study reveals that a wound-induced peptide from PR-1 regulates immune signaling in tomato. Plant Cell. Oct. 2014;26(10):4135-48. doi: 10.1105/tpc.114.131185. Epub Oct. 31, 2014.

Hong et al., Induction by pathogen, salt and drought of a basic class II chitinase mRNA and its in situ localization in pepper (*Capsicum annuum*). Physiol Plant. Apr. 2002;114(4):549-558.

*Primary Examiner* — Julie Ha
(74) *Attorney, Agent, or Firm* — Wolf, Greenfield & Sacks, P.C.

(57) ABSTRACT

A plant defense signaling peptide and applications thereof for inducing systemic immune responses in a plant. In some embodiments, methods for inducing systemic immune responses in a plant comprises applying to the plant a plant defense signaling polypeptide comprising a motif of SEQ ID NO: 1 or SEQ ID NO: 28, or a composition comprising the polypeptide, wherein the polypeptide has up to 100 amino acids in length.

13 Claims, 13 Drawing Sheets

Figure 1:
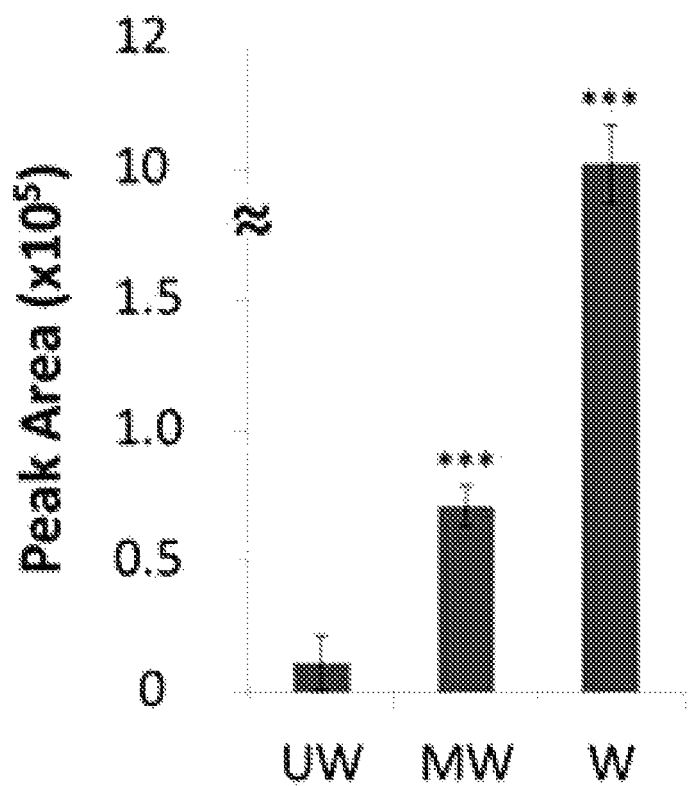

Specification includes a Sequence Listing.

SEQUENCE LISTING

```
<160> NUMBER OF SEQ ID NOS: 84

<210> SEQ ID NO 1
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(9)
<223> OTHER INFORMATION: Xaa can be any naturally occurring amino acid

<400> SEQUENCE: 1

Pro Xaa Gly Asn Xaa Xaa Xaa Xaa Xaa Pro Tyr
1               5                   10
```

```
<210> SEQ ID NO 2
<211> LENGTH: 11
<212> TYPE: PRT
<213> ORGANISM: Solanum lycopersicm

<400> SEQUENCE: 2

Pro Val Gly Asn Trp Ile Gly Gln Arg Pro Tyr
1               5                   10

<210> SEQ ID NO 3
<211> LENGTH: 11
<212> TYPE: PRT
<213> ORGANISM: Solanum lycopersicm

<400> SEQUENCE: 3

Pro Val Gly Asn Trp Val Gly Glu Arg Pro Tyr
1               5                   10

<210> SEQ ID NO 4
<211> LENGTH: 11
<212> TYPE: PRT
<213> ORGANISM: Capsicum annuum

<400> SEQUENCE: 4

Pro Val Gly Asn Trp Val Gly Gln Arg Pro Tyr
1               5                   10

<210> SEQ ID NO 5
<211> LENGTH: 11
<212> TYPE: PRT
<213> ORGANISM: Capsicum frutescens

<400> SEQUENCE: 5

Pro Val Gly Asn Trp Val Gly Gln Arg Pro Tyr
1               5                   10

<210> SEQ ID NO 6
<211> LENGTH: 11
<212> TYPE: PRT
<213> ORGANISM: Solanum tuberosum

<400> SEQUENCE: 6

Pro Val Gly Asn Trp Val Gly Gln Arg Pro Tyr
1               5                   10

<210> SEQ ID NO 7
<211> LENGTH: 11
<212> TYPE: PRT
<213> ORGANISM: Solanum phureja

<400> SEQUENCE: 7

Pro Val Gly Asn Tyr Val Gly Gln Arg Pro Tyr
1               5                   10

<210> SEQ ID NO 8
<211> LENGTH: 11
<212> TYPE: PRT
<213> ORGANISM: Nicotiana glutinosa

<400> SEQUENCE: 8

Pro Pro Gly Asn Phe Val Gly Gln Ser Pro Tyr
1               5                   10
```

```
<210> SEQ ID NO 9
<211> LENGTH: 11
<212> TYPE: PRT
<213> ORGANISM: Nicotiana tabacum

<400> SEQUENCE: 9

Pro Pro Gly Asn Val Ile Gly Gln Ser Pro Tyr
1               5                   10

<210> SEQ ID NO 10
<211> LENGTH: 11
<212> TYPE: PRT
<213> ORGANISM: Vitis vinifera

<400> SEQUENCE: 10

Pro Pro Gly Asn Tyr Val Gly Gln Arg Pro Tyr
1               5                   10

<210> SEQ ID NO 11
<211> LENGTH: 11
<212> TYPE: PRT
<213> ORGANISM: Vitis hybrid cultivar

<400> SEQUENCE: 11

Pro Pro Gly Asn Tyr Val Gly Gln Arg Pro Tyr
1               5                   10

<210> SEQ ID NO 12
<211> LENGTH: 11
<212> TYPE: PRT
<213> ORGANISM: Vitis shuttleworthii

<400> SEQUENCE: 12

Pro Pro Gly Asn Tyr Val Gly Gln Arg Pro Tyr
1               5                   10

<210> SEQ ID NO 13
<211> LENGTH: 11
<212> TYPE: PRT
<213> ORGANISM: Brassica napus

<400> SEQUENCE: 13

Pro Arg Gly Asn Tyr Val Asn Glu Lys Pro Tyr
1               5                   10

<210> SEQ ID NO 14
<211> LENGTH: 11
<212> TYPE: PRT
<213> ORGANISM: Brassica rapa

<400> SEQUENCE: 14

Pro Arg Gly Asn Tyr Val Asn Glu Lys Pro Tyr
1               5                   10

<210> SEQ ID NO 15
<211> LENGTH: 11
<212> TYPE: PRT
<213> ORGANISM: Glycine max

<400> SEQUENCE: 15

Pro Pro Gly Asn Tyr Val Gly Gln Arg Pro Tyr
1               5                   10
```

```
<210> SEQ ID NO 16
<211> LENGTH: 11
<212> TYPE: PRT
<213> ORGANISM: Medicago truncatula

<400> SEQUENCE: 16

Pro Pro Gly Asn Tyr Val Gly Gln Lys Pro Tyr
1               5                   10

<210> SEQ ID NO 17
<211> LENGTH: 11
<212> TYPE: PRT
<213> ORGANISM: Zea mays

<400> SEQUENCE: 17

Pro Pro Gly Asn Phe Arg Gly Gln Arg Pro Tyr
1               5                   10

<210> SEQ ID NO 18
<211> LENGTH: 11
<212> TYPE: PRT
<213> ORGANISM: Oryza sativa

<400> SEQUENCE: 18

Pro Arg Gly Asn Ile Val Gly Arg Arg Pro Tyr
1               5                   10

<210> SEQ ID NO 19
<211> LENGTH: 11
<212> TYPE: PRT
<213> ORGANISM: Arabidopsis thaliana

<400> SEQUENCE: 19

Pro Ala Gly Asn Tyr Ile Gly Ala Arg Pro Tyr
1               5                   10

<210> SEQ ID NO 20
<211> LENGTH: 11
<212> TYPE: PRT
<213> ORGANISM: Arabidopsis thaliana

<400> SEQUENCE: 20

Pro Pro Gly Asn Tyr Ile Gly Gln Lys Pro Tyr
1               5                   10

<210> SEQ ID NO 21
<211> LENGTH: 11
<212> TYPE: PRT
<213> ORGANISM: Arabidopsis thaliana

<400> SEQUENCE: 21

Pro Pro Gly Asn Trp Val Gly Glu Trp Pro Tyr
1               5                   10

<210> SEQ ID NO 22
<211> LENGTH: 11
<212> TYPE: PRT
<213> ORGANISM: Arabidopsis thaliana

<400> SEQUENCE: 22

Pro Pro Gly Asn Tyr Val Gly Glu Lys Pro Tyr
1               5                   10
```

```
<210> SEQ ID NO 23
<211> LENGTH: 11
<212> TYPE: PRT
<213> ORGANISM: Arabidopsis thaliana

<400> SEQUENCE: 23

Pro Pro Gly Asn Tyr Val Gly Glu Lys Pro Tyr
1               5                   10

<210> SEQ ID NO 24
<211> LENGTH: 11
<212> TYPE: PRT
<213> ORGANISM: Arabidopsis thaliana

<400> SEQUENCE: 24

Pro Pro Gly Asn Phe Leu Gly Arg Lys Pro Tyr
1               5                   10

<210> SEQ ID NO 25
<211> LENGTH: 11
<212> TYPE: PRT
<213> ORGANISM: Arabidopsis thaliana

<400> SEQUENCE: 25

Pro Pro Gly Asn Tyr Ala Asn Gln Lys Pro Tyr
1               5                   10

<210> SEQ ID NO 26
<211> LENGTH: 11
<212> TYPE: PRT
<213> ORGANISM: Arabidopsis thaliana

<400> SEQUENCE: 26

Pro Pro Gly Asn Tyr Arg Gly Arg Trp Pro Tyr
1               5                   10

<210> SEQ ID NO 27
<211> LENGTH: 11
<212> TYPE: PRT
<213> ORGANISM: Arabidopsis thaliana

<400> SEQUENCE: 27

Pro Arg Gly Asn Tyr Val Asn Glu Lys Pro Tyr
1               5                   10

<210> SEQ ID NO 28
<211> LENGTH: 15
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(13)
<223> OTHER INFORMATION: Xaa can be any naturally occurring amino acid

<400> SEQUENCE: 28

Cys Asn Tyr Xaa Pro Xaa Gly Asn Xaa Xaa Xaa Xaa Xaa Pro Tyr
1               5                   10                  15
```

```
<210> SEQ ID NO 29
<211> LENGTH: 15
<212> TYPE: PRT
<213> ORGANISM: Solanum lycopersicum

<400> SEQUENCE: 29

Cys Asn Tyr Asp Pro Val Gly Asn Trp Ile Gly Gln Arg Pro Tyr
1               5                   10                  15

<210> SEQ ID NO 30
<211> LENGTH: 15
<212> TYPE: PRT
<213> ORGANISM: Solanum lycopersicum

<400> SEQUENCE: 30

Cys Asn Tyr Asp Pro Val Gly Asn Trp Val Gly Glu Arg Pro Tyr
1               5                   10                  15

<210> SEQ ID NO 31
<211> LENGTH: 15
<212> TYPE: PRT
<213> ORGANISM: Capsicum annuum

<400> SEQUENCE: 31

Cys Asn Tyr Asp Pro Val Gly Asn Trp Val Gly Gln Arg Pro Tyr
1               5                   10                  15

<210> SEQ ID NO 32
<211> LENGTH: 15
<212> TYPE: PRT
<213> ORGANISM: Capsicum frutescens

<400> SEQUENCE: 32

Cys Asn Tyr Asp Pro Val Gly Asn Trp Val Gly Gln Arg Pro Tyr
1               5                   10                  15

<210> SEQ ID NO 33
<211> LENGTH: 15
<212> TYPE: PRT
<213> ORGANISM: Solanum tuberosum

<400> SEQUENCE: 33

Cys Asn Tyr Asp Pro Val Gly Asn Trp Val Gly Gln Arg Pro Tyr
1               5                   10                  15

<210> SEQ ID NO 34
<211> LENGTH: 15
<212> TYPE: PRT
<213> ORGANISM: Solanum Phureja

<400> SEQUENCE: 34

Cys Asn Tyr Asp Pro Val Gly Asn Tyr Val Gly Gln Arg Pro Tyr
1               5                   10                  15

<210> SEQ ID NO 35
<211> LENGTH: 15
<212> TYPE: PRT
<213> ORGANISM: Nicotiana glutinosa

<400> SEQUENCE: 35

Cys Asn Tyr Asp Pro Pro Gly Asn Phe Val Gly Gln Ser Pro Tyr
1               5                   10                  15
```

```
<210> SEQ ID NO 36
<211> LENGTH: 15
<212> TYPE: PRT
<213> ORGANISM: Nicotiana tabacum

<400> SEQUENCE: 36

Cys Asn Tyr Asp Pro Pro Gly Asn Val Ile Gly Gln Ser Pro Tyr
1               5                   10                  15

<210> SEQ ID NO 37
<211> LENGTH: 15
<212> TYPE: PRT
<213> ORGANISM: Vitis vinifera

<400> SEQUENCE: 37

Cys Asn Tyr Asp Pro Pro Gly Asn Tyr Val Gly Gln Arg Pro Tyr
1               5                   10                  15

<210> SEQ ID NO 38
<211> LENGTH: 15
<212> TYPE: PRT
<213> ORGANISM: Vitis hybrid cultivar

<400> SEQUENCE: 38

Cys Asn Tyr Asp Pro Pro Gly Asn Tyr Val Gly Gln Arg Pro Tyr
1               5                   10                  15

<210> SEQ ID NO 39
<211> LENGTH: 15
<212> TYPE: PRT
<213> ORGANISM: Vitis shuttleworthii

<400> SEQUENCE: 39

Cys Asn Tyr Asp Pro Pro Gly Asn Tyr Val Gly Gln Arg Pro Tyr
1               5                   10                  15

<210> SEQ ID NO 40
<211> LENGTH: 15
<212> TYPE: PRT
<213> ORGANISM: Brassica napus

<400> SEQUENCE: 40

Cys Asn Tyr Asp Pro Arg Gly Asn Tyr Val Asn Glu Lys Pro Tyr
1               5                   10                  15

<210> SEQ ID NO 41
<211> LENGTH: 15
<212> TYPE: PRT
<213> ORGANISM: Brassica rapa

<400> SEQUENCE: 41

Cys Asn Tyr Asp Pro Arg Gly Asn Tyr Val Asn Glu Lys Pro Tyr
1               5                   10                  15

<210> SEQ ID NO 42
<211> LENGTH: 15
<212> TYPE: PRT
<213> ORGANISM: Glycine max

<400> SEQUENCE: 42

Cys Asn Tyr Ala Pro Pro Gly Asn Tyr Val Gly Gln Arg Pro Tyr
1               5                   10                  15
```

<210> SEQ ID NO 43
<211> LENGTH: 15
<212> TYPE: PRT
<213> ORGANISM: Medicago truncatula

<400> SEQUENCE: 43

Cys Asn Tyr Asp Pro Pro Gly Asn Tyr Val Gly Gln Lys Pro Tyr
1               5                   10                  15

<210> SEQ ID NO 44
<211> LENGTH: 15
<212> TYPE: PRT
<213> ORGANISM: Zea mays

<400> SEQUENCE: 44

Cys Asn Tyr Asn Pro Pro Gly Asn Phe Arg Gly Gln Arg Pro Tyr
1               5                   10                  15

<210> SEQ ID NO 45
<211> LENGTH: 15
<212> TYPE: PRT
<213> ORGANISM: Oryza sativa

<400> SEQUENCE: 45

Cys Asn Tyr Glu Pro Arg Gly Asn Ile Val Gly Arg Arg Pro Tyr
1               5                   10                  15

<210> SEQ ID NO 46
<211> LENGTH: 15
<212> TYPE: PRT
<213> ORGANISM: Arabidopsis thaliana

<400> SEQUENCE: 46

Cys Asn Tyr Asp Pro Ala Gly Asn Tyr Ile Gly Ala Arg Pro Tyr
1               5                   10                  15

<210> SEQ ID NO 47
<211> LENGTH: 15
<212> TYPE: PRT
<213> ORGANISM: Arabidopsis thaliana

<400> SEQUENCE: 47

Cys Asn Tyr Asp Pro Pro Gly Asn Tyr Ile Gly Gln Lys Pro Tyr
1               5                   10                  15

<210> SEQ ID NO 48
<211> LENGTH: 15
<212> TYPE: PRT
<213> ORGANISM: Arabidopsis thaliana

<400> SEQUENCE: 48

Cys Asn Tyr Asp Pro Pro Gly Asn Trp Val Gly Glu Trp Pro Tyr
1               5                   10                  15

<210> SEQ ID NO 49
<211> LENGTH: 15
<212> TYPE: PRT
<213> ORGANISM: Arabidopsis thaliana

<400> SEQUENCE: 49

Cys Asn Tyr Asp Pro Pro Gly Asn Tyr Val Gly Glu Lys Pro Tyr
1               5                   10                  15

```
<210> SEQ ID NO 50
<211> LENGTH: 15
<212> TYPE: PRT
<213> ORGANISM: Arabidopsis thaliana

<400> SEQUENCE: 50

Cys Asn Tyr Asp Pro Pro Gly Asn Tyr Val Gly Glu Lys Pro Tyr
1               5                   10                  15

<210> SEQ ID NO 51
<211> LENGTH: 15
<212> TYPE: PRT
<213> ORGANISM: Arabidopsis thaliana

<400> SEQUENCE: 51

Cys Asn Tyr Asp Pro Pro Gly Asn Phe Leu Gly Arg Lys Pro Tyr
1               5                   10                  15

<210> SEQ ID NO 52
<211> LENGTH: 15
<212> TYPE: PRT
<213> ORGANISM: Arabidopsis thaliana

<400> SEQUENCE: 52

Cys Asn Tyr Asp Pro Pro Gly Asn Tyr Ala Asn Gln Lys Pro Tyr
1               5                   10                  15

<210> SEQ ID NO 53
<211> LENGTH: 15
<212> TYPE: PRT
<213> ORGANISM: Arabidopsis thaliana

<400> SEQUENCE: 53

Cys Asn Tyr Tyr Pro Pro Gly Asn Tyr Arg Gly Arg Trp Pro Tyr
1               5                   10                  15

<210> SEQ ID NO 54
<211> LENGTH: 15
<212> TYPE: PRT
<213> ORGANISM: Arabidopsis thaliana

<400> SEQUENCE: 54

Cys Asn Tyr Asp Pro Arg Gly Asn Tyr Val Asn Glu Lys Pro Tyr
1               5                   10                  15

<210> SEQ ID NO 55
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 55

Cys Asn Tyr Xaa
1

<210> SEQ ID NO 56
<211> LENGTH: 6
<212> TYPE: PRT
<213> ORGANISM: Artificial Sequence
<220> FEATURE:
<223> OTHER INFORMATION: Synthetic polypeptide
```

```
<400> SEQUENCE: 56

Cys Asn Tyr Asp Pro Val
1               5

<210> SEQ ID NO 57
<211> LENGTH: 159
<212> TYPE: PRT
<213> ORGANISM: Solanum lycopersicum

<400> SEQUENCE: 57

Met Gly Leu Phe Asn Ile Ser Leu Leu Leu Thr Cys Leu Met Val Leu
1               5                   10                  15

Ala Ile Phe His Ser Cys Glu Ala Gln Asn Ser Pro Gln Asp Tyr Leu
                20                  25                  30

Ala Val His Asn Asp Ala Arg Ala Gln Val Gly Val Gly Pro Met Ser
            35                  40                  45

Trp Asp Ala Asn Leu Ala Ser Arg Ala Gln Asn Tyr Ala Asn Ser Arg
    50                  55                  60

Ala Gly Asp Cys Asn Leu Ile His Ser Gly Ala Gly Glu Asn Leu Ala
65                  70                  75                  80

Lys Gly Gly Gly Asp Phe Thr Gly Arg Ala Ala Val Gln Leu Trp Val
                85                  90                  95

Ser Glu Arg Pro Ser Tyr Asn Tyr Ala Thr Asn Gln Cys Val Gly Gly
                100                 105                 110

Lys Lys Cys Arg His Tyr Thr Gln Val Val Trp Arg Asn Ser Val Arg
            115                 120                 125

Leu Gly Cys Gly Arg Ala Arg Cys Asn Asn Gly Trp Trp Phe Ile Ser
    130                 135                 140

Cys Asn Tyr Asp Pro Val Gly Asn Trp Ile Gly Gln Arg Pro Tyr
145                 150                 155

<210> SEQ ID NO 58
<211> LENGTH: 18
<212> TYPE: PRT
<213> ORGANISM: Solanum lycopersicum

<400> SEQUENCE: 58

Ala Val Gln Ser Lys Pro Pro Ser Lys Arg Asp Pro Pro Lys Met Gln
1               5                   10                  15

Thr Asp

<210> SEQ ID NO 59
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 59

Pro Ala Ala Ala Tyr Ile Gly Ala Arg Ala Tyr
1               5                   10

<210> SEQ ID NO 60
<211> LENGTH: 22
<212> TYPE: PRT
<213> ORGANISM: Artificial Sequence
<220> FEATURE:
<223> OTHER INFORMATION: Synthetic polypeptide
```

-continued

<400> SEQUENCE: 60

Gln Arg Leu Ser Thr Gly Ser Arg Ile Asn Ser Ala Lys Asp Asp Ala
1               5                   10                  15

Ala Gly Leu Gln Ile Ala
            20

<210> SEQ ID NO 61
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 61

Cys Asn Tyr Asp
1

<210> SEQ ID NO 62
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 62

Cys Asn Ala Asp
1

<210> SEQ ID NO 63
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 63
ctccgtcttc cacttcagg                                            19

<210> SEQ ID NO 64
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 64
tcagttgtca aaccagtagg g                                         21

<210> SEQ ID NO 65
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 65
actcttgccg actacaacat cc                                        22

<210> SEQ ID NO 66
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 66
ctccttacga agcctctgaa cc				22

<210> SEQ ID NO 67
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 67
cttcttccaa cttcctttg				19

<210> SEQ ID NO 68
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 68
tgttttcctt cgcacatc				18

<210> SEQ ID NO 69
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 69
aattatccat catggctgtt cac				23

<210> SEQ ID NO 70
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 70
cctttttgga tcagattctc ctt				23

<210> SEQ ID NO 71
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 71
aggcagtttc ctataggggc ta				22

<210> SEQ ID NO 72
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 72
tcgaccatca ggtcttcttc c				21

```
<210> SEQ ID NO 73
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 73
atgggttctc cacaagagac                                              20

<210> SEQ ID NO 74
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 74
gaagcttgcg atgtcatcaa                                              20

<210> SEQ ID NO 75
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 75
ctcatatgag acgtcgagaa g                                            21

<210> SEQ ID NO 76
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 76
ggaaacaaga agatgcagta cttaa                                        25

<210> SEQ ID NO 77
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 77
caaataacag gagcgcagcc                                              20

<210> SEQ ID NO 78
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 78
gttacttcct ttgagggcat                                              20

<210> SEQ ID NO 79
<211> LENGTH: 19
<212> TYPE: DNA
<213> ORGANISM: Artificial Sequence
<220> FEATURE:
<223> OTHER INFORMATION: Synthetic polynucleotide
```

```
<400> SEQUENCE: 79
tcagcacctc tggaccttt                                                   19

<210> SEQ ID NO 80
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 80
gctcctgaag gctctgtta                                                   19

<210> SEQ ID NO 81
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 81
ttttggtcga ggtcctatcc                                                  20

<210> SEQ ID NO 82
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 82
gtaatgacat cgtgtgccga                                                  20

<210> SEQ ID NO 83
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 83
aaatggattg tgcatcaaac tggga                                            25

<210> SEQ ID NO 84
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 84
agccacccca gttgagaatc aaca                                             24
```

PLANT DEFENSE SIGNALING PEPTIDES AND APPLICATIONS THEREOF

RELATED APPLICATIONS

The present application is a national stage filing under 35 U.S.C. § 371 of International Application No. PCT/US2015/057621, filed Oct. 27, 2015, which claims priority under 35 U.S.C. § 119(e) to U.S. Provisional Application No. 62/068,987, filed on Oct. 27, 2014, the contents of each of which are hereby incorporated by reference in their entirety.

TECHNOLOGY FIELD

The present invention relates to a novel plant defense signaling peptide and applications thereof.

BACKGROUND OF THE INVENTION

All multicellular organisms have evolved mechanisms to perceive and respond to extracellular chemical signals. Among them, peptides are the most common mediators of intercellular interactions in animals because they provide great variety in their sequences, lengths and/or post-translational modifications (PTMs) to represent different physiological responses (Boller, 2005). In contrast to peptide discovery in animals, only a few signaling peptides have been identified in plants (Farrokhi et al., 2008a; Butenko et al., 2009). It is expected that most of the endogenous plant signaling peptides that play prominent roles in intercellular communication are still undiscovered. Because the complete sequencing of the *Arabidopsis* genome has revealed that plants have up to ten times as many predicted peptide receptors (Shiu and Bleecker, 2003) and transporters (Initiative, 2000) as animals. Moreover, among the currently identified peptides in plants, only relatively few have been found to function in defense signaling. This is mainly due to the fact that defense signaling peptides are mostly derived from the selective action of proteases on larger precursor proteins, are expressed at low levels, and are highly dynamic.

It is already known that tomato wounding can induce an anti-herbivore response, which is regulated by the peptide hormone systemin, and the small molecule hormone jasmonic acid (JA) and its methyl ester, MeJA (Pearce et al., 1991; Orozco-Cardenas et al., 2001). Systemin was the first identified signaling peptide and also the first confirmed peptide elicitor of damage associated molecular patterns (DAMPs) in plant. It is expected that several signaling peptides are involved in combating herbivore and pathogen attack (Cheong et al., 2002; Francia et al., 2007; Chassot et al., 2008), but the details of the regulation of anti-herbivore and anti-pathogen responses by peptides during wounding stress still await elucidation. Several DAMP peptides have been discovered in other plant species and suggested to be bioactive in tomato (Boller and Felix, 2009b; Campos et al., 2014); these include HypSys (Pearce et al., 2001a; Narvaez-Vasquez et al., 2007), RALF (Pearce et al., 2001b) and Pep1 (Huffaker et al., 2006; A. P. Trivilin, 2014). Pep1 was clearly identified to be pathogen-related in *Arabidopsis* and its putative precursor in tomato was recently found to involve in the anti-pathogen response (A. P. Trivilin, 2014). However, its endogenous level in tomato has not yet been proved to be induced by tissue damage or MeJA, a potent inducer of systemic wound signaling and response in tomato (Scheer and Ryan, 1999). To our knowledge, no study to date has quantitatively profiled the global change in cellular peptide expression in plants before and/or after the induction of stress responses.

There is a need to identify new defense signaling peptides in plants which not only to advance plant stress biology, but also to aid in the development of alternative ways to improve stress tolerance or resistance for better crop productivity and minimization of the use of agrochemicals (Pearce et al., 1991; Pearce et al., 2001a; Huffaker et al., 2006).

SUMMARY OF THE INVENTION

In this invention, it is unexpectedly found that a peptide elicitor derived from tomato pathogenesis-related protein 1 (PR-1) can regulate plant immune responses against biological threats e.g. pathogen infection, which contains a conserved 11-amino acid signaling peptide motif (PxGNxxxxxPY) (SEQ ID NO: 1) across many plant species. It is found that a peptide having such motif acts as a plant defense signaling peptide, which can increase plant defense activity by increasing immune responses such as production of $H_2O_2$ or plant hormones or activation of one or more anti-herbivore or anti-pathogen genes when applied to plant. It is also found that a CNYx motif is critical to be recognized by an endogenous protease to cleave a precursor (e.g. a full length of PR-1) to generate an active plant defense signaling peptide. Therefore, a peptide with a 15-amin acid motif (CNYxPxGNxxxxxPY) (SEQ ID NO: 28) can also be applied to plant where a plant defense signaling peptide (with the PxGNxxxxxPY motif, SEQ ID NO: 1) can be generated through a specific cleavage by an endogenous protease. Further, a peptide having a CNYx motif (SEQ ID NO: 55) but lacking the 11-amino acid signaling peptide motif (PxGNxxxxxPY) (SEQ ID NO: 1) can be used as a negative regulator to down regulate the defense activity in plants.

Therefore, in one aspect, the present invention provides an isolated plant defense signaling polypeptide comprising an 11-amino acid motif of SEQ ID NO: 1 (PxGNxxxxxPY).

In some embodiments, the plant defense signaling polypeptide of the invention is selected from the group consisting of SEQ ID NO: 2-27.

The present invention also provides an isolated plant defense signaling polypeptide comprising a 15-amin acid motif of SEQ ID NO: 28 (CNYxPxGNxxxxxPY).

In some embodiments, the plant defense signaling polypeptide of the invention is selected from the group consisting of SEQ ID NO: 29-54.

In another aspect, the present invention relates to a composition comprising a plant defense signaling polypeptide as described herein.

In still another aspect, the present invention relates to a method for treating a plant to increase plant defense activity, comprising applying to said plant a plant defense signaling polypeptide or a composition comprising a plant defense signaling polypeptide as described herein.

In some embodiments, the defense activity includes anti-herbivore or anti pathogen responses, for example, production of hydrogen peroxide ($H_2O_2$), generation of a plant hormone, e.g. jasmonate (JA), JA conjugated with amino acid isoleucine (JA-Ile) or salicylic acid (SA), or expression of an anti-herbivore or anti-pathogen protein, e.g. proteinase inhibitor 1 (PI-1), proteinase inhibitor 2 (PI-2), pathogenesis-related protein 1b (PR-1b, CAPE1 precursor gene), beta-1,3-glucanase (PR-2), cys protease (PR-7), class ii chitinase (Chi2; 1), ethylene response factor 5 (ERF5) or avrpto-dependent pto-interacting protein 3 (Adi3).

In some embodiments, the defense activity is not only exist in local treated site, but also systemic untreated leaves, for example, generation of a plant hormone, salicylic acid (SA), or expression of anti-pathogen proteins, e.g. pathogenesis-related protein 1b (PR-1b, CAPE1 precursor gene) and ethylene response factor 5 (ERF5).

In some embodiments, the CNYx is a core structure for designing protease inhibitor to prevent processing and decrease defense activity.

In some embodiments, the plants to which the inventive method can be applied include both monocotyledon and dicotyledon. Examples of monocotyledon includes but not limited to rice, barley, wheat, rye, oat, corn, bamboo, sugar cane, onion, leek and ginger. Examples of the dicotyledons include, but are not limited to *Arabidopsis thaliana*, eggplant, tobacco plant, red pepper, tomato, burdock, crown daisy, lettuce, balloon flower, spinach, chard, potato, celery, carrot, water dropwort, parsley, Chinese cabbage, cabbage, radish, watermelon, melon, cucumber, pumpkin, gourd, strawberry, soybean, mung bean, kidney bean, and pea.

In some embodiments, the plant defense signaling polypeptide is present in the composition at a concentration of about 50 nM or more, 100 nM or more, 150 nM or more, 200 nM or more or 250 nM or more.

In some embodiments, the plant defense responses can be induced within 2 hours and last for more than 24 hours after the composition is sprayed to a plant.

In some embodiments, the defense signaling polypeptide of the invention can be applied in combination with salt treatment to enhance the anti-pathogen activity. Therefore, also provided is a combination comprising the defense signaling polypeptide as described herein and salt, and a method of the present invention as described herein can further comprise treating the plant with salt, in addition to applying the defense signaling polypeptide as described herein to the plant. In certain embodiments, the defense signaling polypeptide is mixed with a proper amount of salt and the mixture (in a form of solution or powder) is applied to the plant, e.g. by spray or immersion. A certain example of the salt is NaCl, at a concentration of around 25 mM or more, 50 mM or more, 100 mM or more, 150 mM or more.

In a further aspect, the present invention relates to a method of down regulating a defense activity in a plant, comprising treating the plant with a peptide having a CNYx motif but lacking a 11-amino acid signaling peptide motif (PxGNxxxxxPY) in an amount to effectively reduce or block the enzymatic activity of a protease in cleaving a precursor peptide (e.g. CNYxPxGNxxxxxPY or the full length of PR-1) to generate a plant defense signaling peptide having the 11-amino acid motif of PxGNxxxxxPY as described above.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1 shows validation of the endogenous CAPE1 identity and the expression level triggered by wounding and wounding plus MeJA. The quantitative analysis of endogenous CAPE1 expression level in unwounded (UW), mechanically wounded (MW) and wounded plus MeJA (W) treated tomato using LC-SRM-MS. The data represented the means and SD of three biological samples. The statistically significant differences between the UW, MW and W samples are indicated with *** ($P<0.001$) based on Student's t-test.

FIG. 2 shows study of CAPE1 bioactivities in the triggering of leaf tissue $H_2O_2$ production. Detached tomato leaves were treated with water (Control), mechanical wounding (MW), 1.25 mM MeJA, 250 nM systemin and 250 nM CAPE1 peptide for 4 hours, respectively. After the treatment, 1 mg/ml of diaminobenzidine (DAB) was applied to visualize $H_2O_2$ accumulation. Experiments were presented by three biological repeats to confirm for obtaining the similar results.

FIG. 3 shows anti-pathogen and anti-herbivore defense genes of tomato plants induced by spraying with CAPE1. Relative expression of anti-herbivore and anti-pathogen defense genes were quantified by comparing the expression levels in untreated plants with plants treated with water or 250 nM CAPE1 for 4, 8, and 24 hours (n=5 for each time point). The internal control EF-1$\alpha$ was used for normalization. All statistically significant differences between the CAPE1- and water-treated samples are indicated with * ($P<0.05$),  ($P<0.01$) or * ($P<0.001$) based on Student's t-test.

FIG. 4 shows anti-herbivore and anti-pathogen defense responses of tomato plants induced by spraying with CAPE1. (a) Changes of the larval sizes after feeding with water or 250 nM CAPE1 treated tomato leaves. The larval weights of thirty larvae were recorded each day. (b) The Pst DC3000 infection phenotypes of the plants presprayed with water or 100 nM CAPE1 peptide for 2 hours (n=3) prior to pathogen inoculation. The bacterial numbers, presented as log colony-forming units (Log CFU) per g leaf tissue, represent the means and SD of three biological samples. All statistically significant differences between the CAPE1- and water-treated samples are indicated with * ($P<0.05$) or *** ($P<0.001$) based on Student's t-test.

FIG. 5 shows induction of jasmonate hormone accumulation by CAPE1 and systemin in excised plants. The level of JA and JA-Ile induced by CAPE1 and systemin. The plants treated with 10 mM phosphate buffer (buffer), 365 nM systemin (Sys) or 365 nM CAPE1 in buffer through the cut stem for 2 and 4 hours (n=3). The quantity of JA and JA-Ile were quantified by LC-SRM-MS and calculated by the abundance of spiked standard $H_2JA$. Data represent the means and SD of three independent biological replicates. A statistically significant difference compared with the correspondingly treated water (or buffer) samples is indicated with  ($P<0.01$) or * ($P<0.001$) based on Student's t-test.

FIG. 6 shows the SA accumulation, anti-pathogen genes and responses induced by CAPE1 and flg22 in tomato. (a) The level of SA induced by CAPE1 and flg22. The excised plants were pretreated with 10 mM phosphate buffer (buffer) or 365 nM CAPE1 or 365 nM flg22 in buffer through the cut stem for 8 hours (n=3). The quantity of SA was quantified by LC-SRM-MS and calculated based on the abundance of spiked SA isotopic standard ($d_6$-SA). (b) The relative expression of WRKY53 and PR-1b were quantified by comparing the expression levels in untreated detached leaves with the detached leaves treated with water, 250 nM CAPE1 or 250 nM flg22 for 2 hours (n=4). The internal control Ubi3 was used for normalization. (c) The Pst DC3000 infection phenotypes for plants presprayed with water, 100 nM CAPE1 or 100 nM flg22 peptide for 2 hours (n=3) prior to the pathogen inoculation. The infection symptoms were observed 4 days after inoculation. The bacterial numbers were calculated 4 days after inoculation and represented as log colony-forming units (Log CFU) per g leaf tissue. Data represent the means and SD of three biological samples. A statistically significant difference compared with the correspondingly treated water (or buffer) samples is indicated with  (P<0.01) or * (P<0.001) based on Student's t-test.

Figure 7:
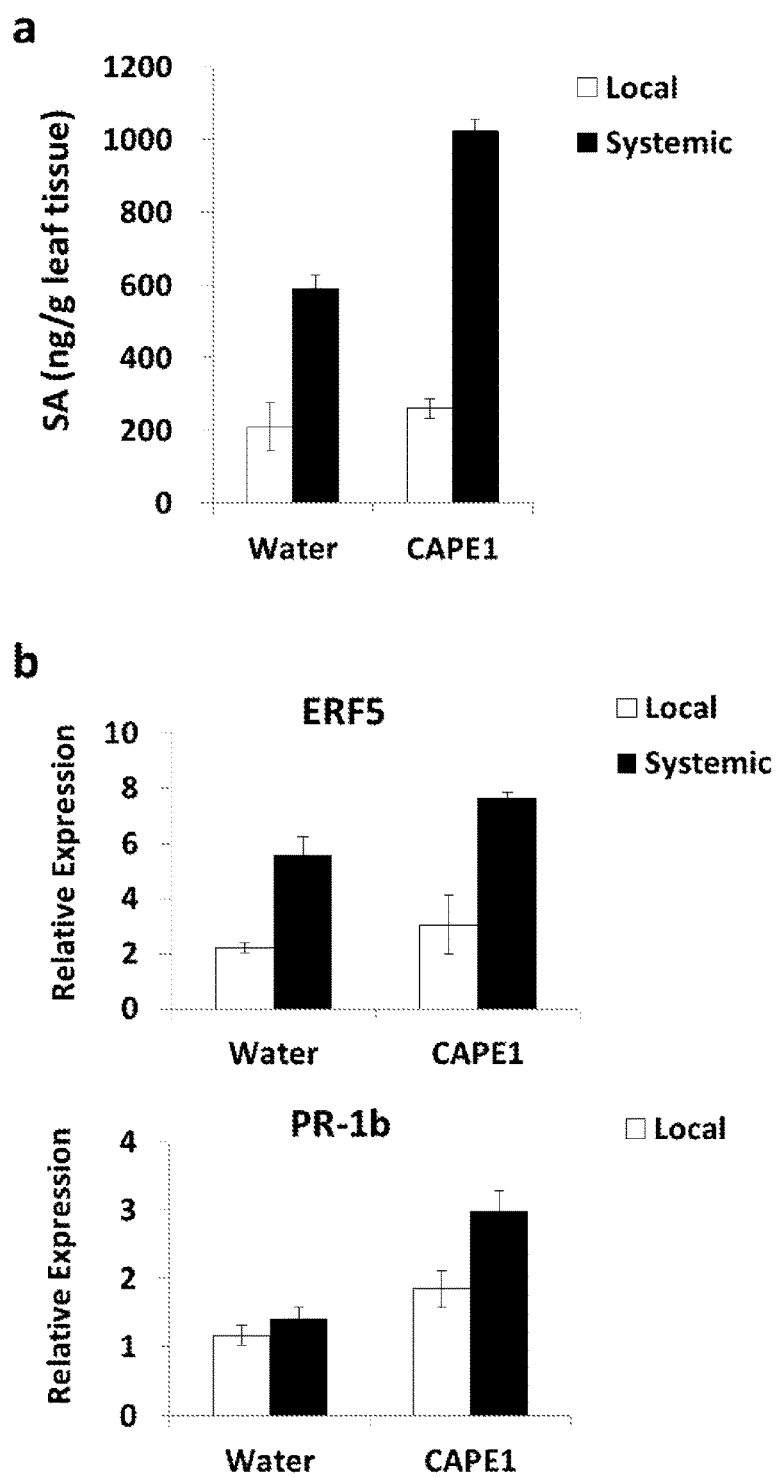

FIG. 7 shows CAPE1 can trigger the systemic immune response in tomato. The plants were separated to local and systemic leaves, the systemic leaves were covered by plastic bags to prevent treatment and the local leaves were treated with water or 250 nM CAPE1 for 24 hours. (a) The levels of SA were induced by CAPE1 in local and systemic tomato leaves. The quantities of SA were quantified by LC-SRM-MS and calculated by the abundance of spiked standard d6SA. (b) The relative expression of ERF5 and PR-1b was quantified by comparing the expression levels in untreated leaves with leaves treated with water, 250 nM CAPE1 for 24 hours. The internal control Ubi3 was used for normalization.

Figure 8:
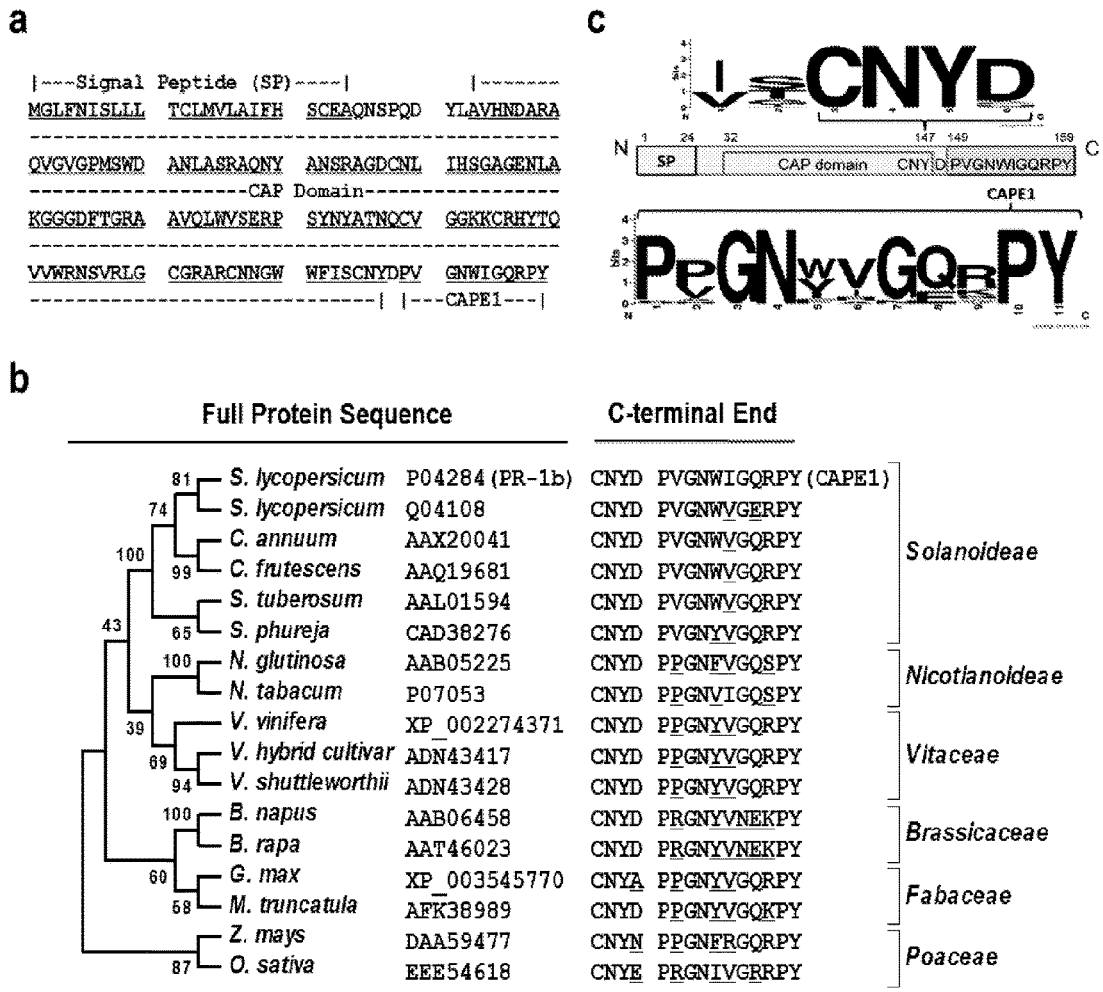

FIG. 8 shows identification of conserved CAPE sequences and proproteins in diverse species based on tomato CAPE1. (a) The sequence and the classified motifs of CAPE1 preprotein (Tomato PR-1b) (SEQ ID NO: 57). (h) Phylogenetic analysis of 17 selected CAPE proproteins generated by MEGA5.2 using the Maximum Likelihood method based on the Whelan and Goldman model. Bootstrap values set to 1,000 replicates. (c) The sequence identities and logo illustration of 30 CAPE1 homologs generated by Weblogo (weblogo.berkelev.edu/logo.cgi). SP: Signal Peptide, CAP Domain: cysteine-rich secretory proteins, antigen 5, and pathogenesis-related 1 proteins domain.

Figure 9:
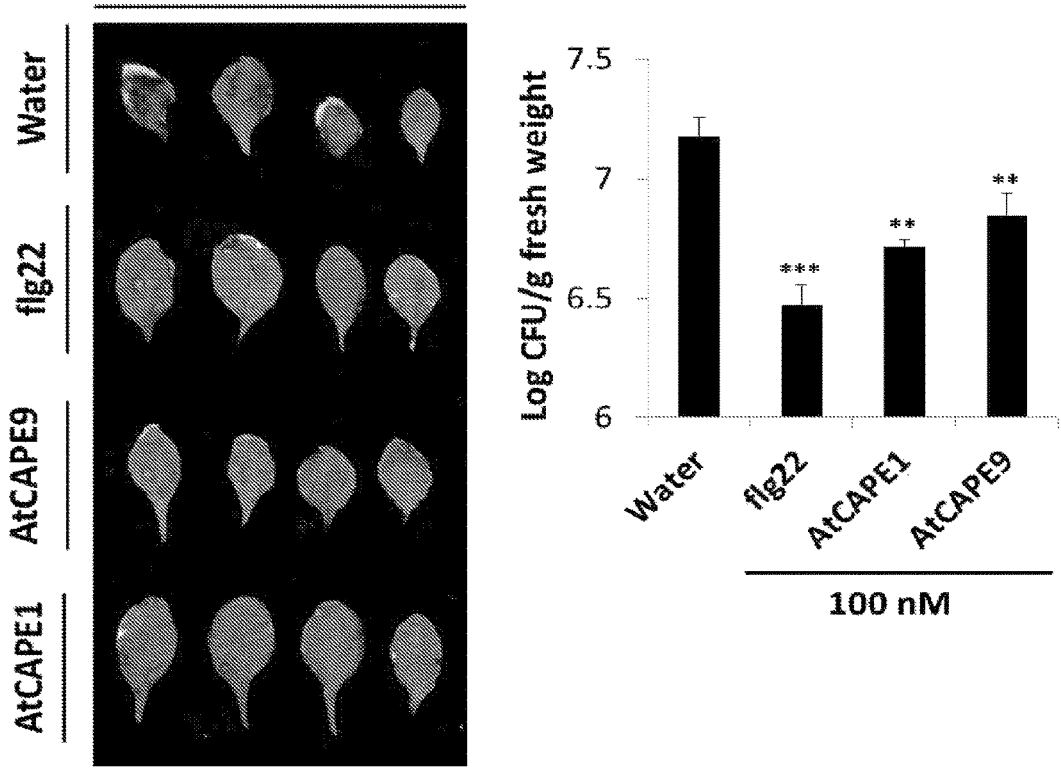

FIG. 9 shows identification of CAPE homologs in Arabidopsis and the anti-pathogen activity of AtCAPE1 (SEQ ID NO: 19) and AtCAPE9. (a) The putative AtCAPE peptides derived from the CAP proteins in Arabidopsis containing a conserved cleavage (CNYx) (SEQ ID NO: 55) and a signaling peptide (PxGNxxxxxPY) motif (SEQ ID NO: 28). According to their identities, the highest identity of CAPE is derived from At4g33730, designated AtCAPE1; the lowest identity of CAPE is derived from At2g14610 (PR1), designated AtCAPE9. Red characters indicated different amino acids compared to SolCAPE1 (b) The Pst DC3000 infection phenotypes for the plants presprayed with water, 100 nM AtCAPE1, AtCAPE9 or 100 nM flg22 peptide for 2 hours (n=3) prior to pathogen inoculation. The infection symptoms were observed 4 days after inoculation. The bacterial numbers were calculated 4 days after inoculation and are represented as log colony-forming units (Log CFU) per g leaf tissue. Data represent the means and SD of three biological samples. A statistically significant difference compared with the corresponding water-treated samples is indicated with  (P<0.01) or * (P<0.001) based on Student's t-test.

Figure 10:
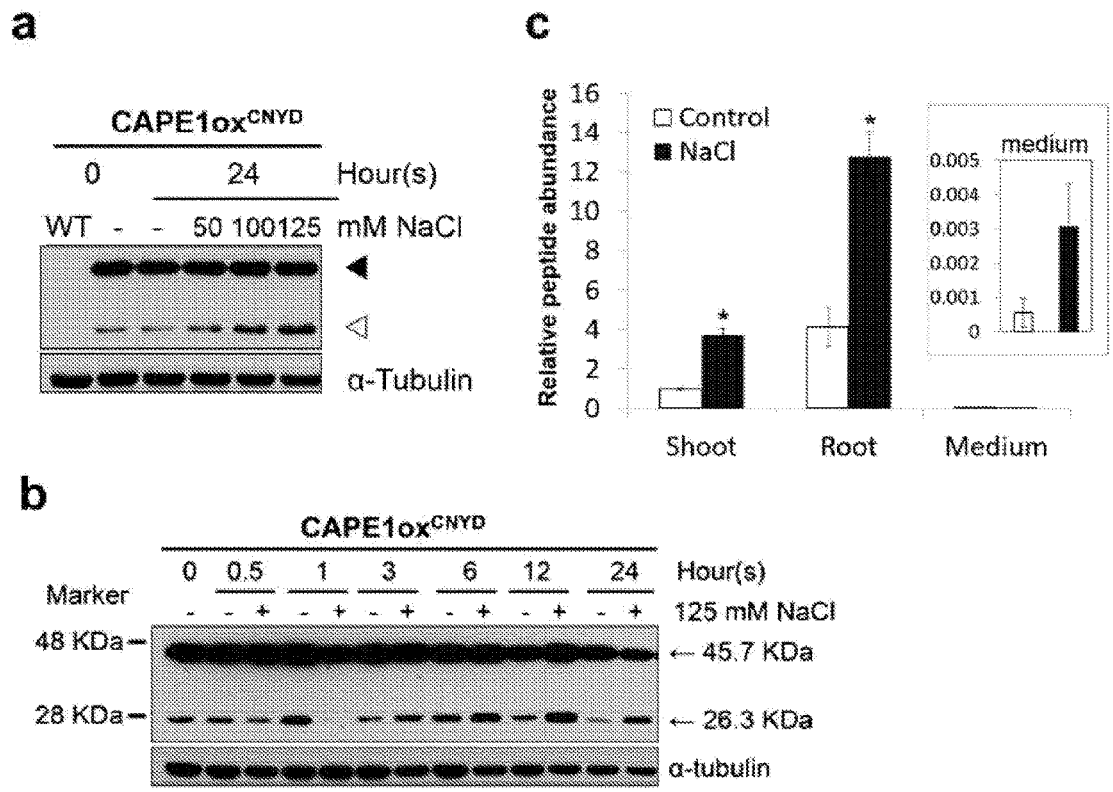

FIG. 10 shows the AtCAPE1 production can be induced by salt in Arabidopsis. (a) Production of the precursor PROAtCAPE1 and the AtCAPE1 peptide was cleaved from PROAtCAPE1 in CAPE1oxCNYD without (−) or with different NaCl concentration for 24 hours. The putative CAPE is shown in red. The numbers indicate the predicted molecular weight of precursor protein tagged with eYFP (45.7 kDa) and the cleaved precursor tagged with eYFP (26.3 kDa). (b) Protein extracts from the transgenic lines (CAPE1oxCNYD) harbouring the AtCAPE1-eYFP fusion grown with (+) and without (−) 125 mM NaCl for the indicated times were subjected to western blot analysis. The upper and lower bands with approximate size of 45.7 KDa and 26.3 KDa represent the expected size of the PROAtCAPE1-eYFP fusion protein and the AtCAPE1-eYFP fusion protein, respectively. The fusion proteins were detected by anti-GFP antibody. α-tubulin, loading control. (c) Relative level of endogenous AtCAPE1 in shoots and roots. Seedlings grown for 24 h without (½ MS) and with 125 mM NaCl were subjected to quantitative LC-MS/MS analysis. IS, internal standard. The average values from two biological repeats are shown. Error bars, means±SE. Asterisks indicate statistically significant differences between salt treated and untreated samples (Student's t-test; **P≤0.01).

Figure 11:
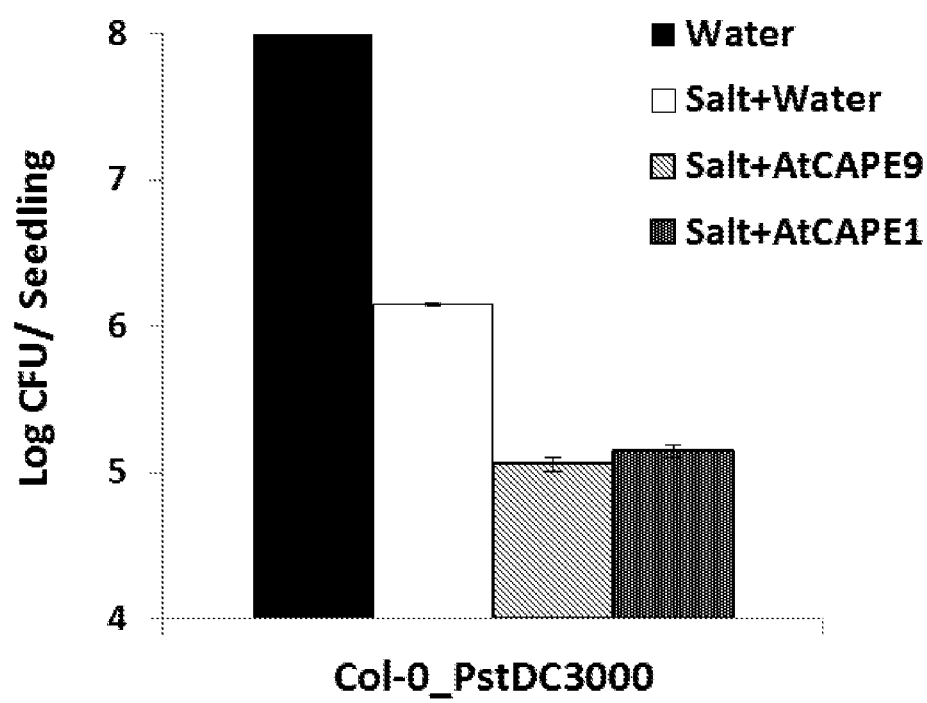

FIG. 11 shows salt treatment can induce AtCAPEs for enhancing plant immune responses in Arabidopsis. 5 days Arabidopsis seedlings treated with 50 mM NaCl for 24 hours and following the treatment of with or without 250 nM AtCAPE1 for 6 hours. The infection symptoms were observed 4 days after Pst DC3000 inoculation. The bacterial numbers were calculated 7 days after inoculation and represented as log colony-forming units (Log CFU) per g leaf tissue. Data represent the means and SD of three biological samples.

Figure 12:
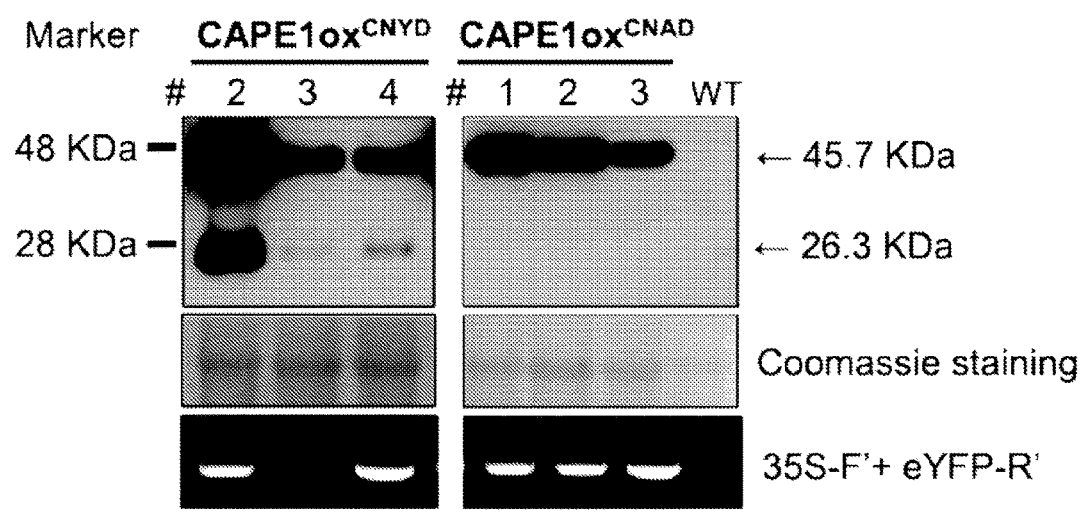

FIG. 12 shows the production of the precursor PROAtCAPE1 and the cleaved PROAtCAPE1 in CAPE1oxCNYD and CAPE1oxCNAD transgenic plants, where eYFP was fused to PROAtCAPE1 containing wild type (CNYD, SEQ ID NO: 61) and the mutated (CNAD, SEQ ID NO: 62) junction sequence, respectively. T3 seedlings derived from independent transgenic lines were sampled for western blotting with anti-GFP antibody. Coomassie blue staining was used for protein loading control.

Figure 13:
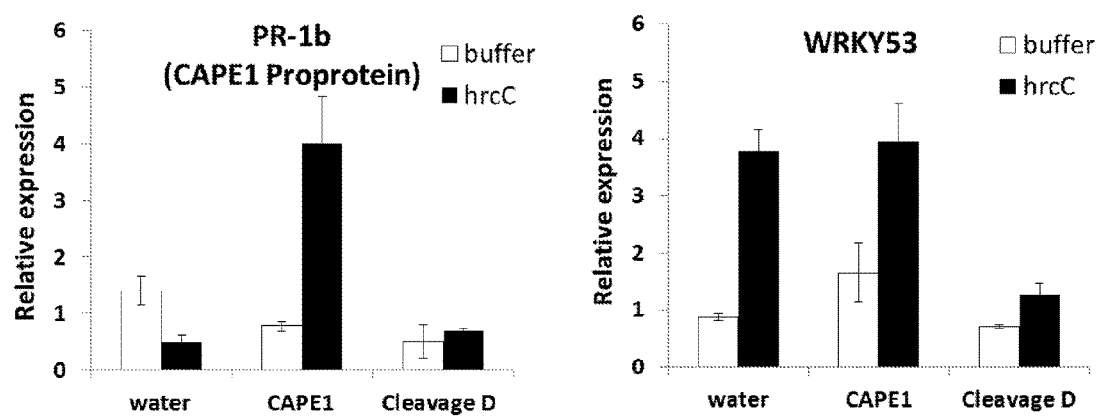

FIG. 13 shows the cleavage motif (CNYX.) of PR-1b inhibited defense gene expression in tomato. Relative expression levels of PR-1b and WRKY53 were analyzed by qRT-PCR 2 h after challenge of $10^7$ cfu/mL Pst DC3000 hrcC⁻ or buffer in tomato leaves, which was pretreated with water, 100 nM CAPE1 or 1 μM CNYDPV for 2 h, respectively.

DETAILED DESCRIPTION OF THE INVENTION

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a component" includes a plurality of such components and equivalents thereof known to those skilled in the art.

The term "comprise" or "comprising" is generally used in the sense of include/including which means permitting the presence of one or more features, ingredients or components. The term "comprise" or "comprising" encompasses the term "consists" or "consisting of."

The terms "polypeptide" and "peptide" as used herein are interchangeable. As used herein, the term "defense signaling peptide/polypeptide" refers to a peptide or a polypeptide of about 10 or more amino acid residues in length that has substantial defense signaling peptide activity e.g. activation of anti-herbivore or anti pathogen genes or induction of plant hormones to enhance immune activities. Preferably, defense signaling peptides or polypeptides up to about 150 amino acid residues or 100, or 90, or 80, or 70, or 60, or 50, or 40, or 30, or 20, or 15 amino acid residues are included in the defense signaling peptides or polypeptides as described herein.

In this study, an MS-based peptidomics approach using a hypothetical peptide database combining a target-decoy search strategy and differential database match scoring is developed to discover defense signaling peptides. This platform is demonstrated by the identification of defense peptides induced by wounding plus methyl jasmonate (MeJA) treatment in *Solanum lycopersicum* (tomato). Using this platform, several peptides including systemin have been identified and quantified to be wounding-plus MeJA-induced. One of the peptides induced by wounding only or wounding plus MeJA is found to activate immune signals for defense against biological threats.

Accordingly, the present invention provides an isolated peptide having a conserved motif of SEQ ID NO: 1 (PxGNxxxxxPY) which can act as a defense signaling peptide. The present invention provides also provides an isolated peptide having a conserved motif of SEQ ID NO: 28 (CNYxPxGNxxxxxPY) which can also be applied to plants where a specific cleavage by a proteolytic enzyme can occur such that the defense signaling peptide having SEQ ID NO: 1 is generated to provide a desired defense activity in the plants. See Table 1.

TABLE 1

| Motif | SEQ IN NO |
|---|---|
| PxGNxxxxxPY | 1 |
| CNYxPxGNxxxxxPY | 28 |

In some embodiments, the plant defense signaling peptide as described herein is selected from the group consisting of SEQ ID NO: 2-27 or SEQ ID NO: 29-54. See Table 2.

TABLE 2

| Plant species | Accession no. | Sequence | SEQ IN NO |
|---|---|---|---|
| S. Lycoperiscum | P04284 (PR1b) | PVGNWIGQRPY | 2 |
| | | CNYD PBGNWIGQRPY | 29 |
| S. Lycoperiscum | Q04108 | PVGNWVGERPY | 3 |
| | | CNYD PVGNWVGERPY | 30 |
| C. annuum | AAX20041 | PVGNWVGQRPY | 4 |
| | | CNYD PVGNWVGQRPY | 31 |
| C. frutescens | AAQ19681 | PVGNWVGQRPY | 5 |
| | | CNYD PVGNWVGQRPY | 32 |
| S. tuberosum | AAL01594 | PVGNWVGQRPY | 6 |
| | | CNYD PVGNWVGQRPY | 33 |
| S. phrueja | CAD38276 | PVGNYVGQRPY | 7 |
| | | CNYD PVGNYVGQRPY | 34 |
| N. glutinosa | AAB05225 | PPGNFVGQSPY | 8 |
| | | CNYD PPGNFVGQSPY | 35 |
| N. tabacum | P07053 | PPGNVIGQSPY | 9 |
| | | CNYD PPGNVIGQSPY | 36 |
| V, vinifera | XP_002274371 | PPGNYVGQRPY | 10 |
| | | CNYD PPGNYVGQRPY | 37 |
| V. hybrid cyltiar | ADN43417 | PPGNYVGQRPY | 11 |
| | | CNYD PPGNYVGQRPY | 38 |
| V. shuttleworthii | ADN43428 | PPGNYVGQRPY | 12 |
| | | CNYD PPGNYVGQRPY | 39 |
| B. napus | AAB06458 | PRGNYVNEKPY | 13 |
| | | CNYD PRGNYVNEKPY | 40 |
| B. rapa | AAT46023 | PRGNYVNEKPY | 14 |
| | | CNYD PRGNYVNEKPY | 41 |
| G. max | XP_003545770 | PPGNYVGQRPY | 15 |
| | | CNYD PPGNYVGQRPY | 42 |
| M. truncatula | AFK38989 | PPGNYVGQKPY | 16 |
| | | CNYD PPGNYVGQKPY | 43 |
| Z. mays | DAA59477 | PPGNFRGQRPY | 17 |
| | | CNYD PPGNFRGQRPY | 44 |
| O. sativa | EE54618 | PRGNIVGRRPY | 18 |
| | | CNYD PRGNIVGRRPY | 45 |
| Arabidopsis | AT4G33730.1 | PAGNYIGARPY | 19 |
| | | CNYD PAGNYIGARPY | 46 |

TABLE 2-continued

| Plant species | Accession no. | Sequence | SEQ IN NO |
|---|---|---|---|
| Arabidopsis | AT4G25780.1 | PPGNYIGQKPY<br>CNYD PPGNYIGQKPY | 20<br>47 |
| Arabidopsis | AT4G33720.1 | PPGNWVGEWPY<br>CNYD PPGNWVGEWPY | 21<br>48 |
| Arabidopsis | AT4G25790.1 | PPGNYVGEKPY<br>CNYD PPGNYVGEKPY | 22<br>49 |
| Arabidopsis | AT4G57625.1 | PPGNYVGEKPY<br>CNYD PPGNYVGEKPY | 23<br>50 |
| Arabidopsis | AT4G30320.1 | PPGNFLGRKPY<br>CNYD PPGNFLGRKPY | 24<br>51 |
| Arabidopsis | AT2G14580.1<br>(PRB1) | PPGNYANQKPY<br>CNYD PPGNYANQKPY | 25<br>52 |
| Arabidopsis | AT5G26130.1 | PPGNYRGRWPY<br>CNYD PPGNYRGRWPY | 26<br>53 |
| Arabidopsis | AT2G14610.1<br>(PR1) | PRGNYVNEKPY<br>CNYD PRGNYVNEKPY | 27<br>54 |

A plant defense signaling peptide as described herein may be produced chemical synthesis using techniques well known in the chemistry of proteins such as solid phase synthesis or synthesis in homogenous solution.

Alternatively, the peptide of the present invention may be prepared using recombinant techniques. In this regard, a recombinant nucleic acid comprising a nucleotide sequence encoding a polypeptide of the present invention and host cells comprising such recombinant nucleic acid are provided. The host cells may be cultured under suitable conditions for expression of the polypeptide of interest. Expression of the polypeptides may be constitutive such that they are continually produced or inducible, requiring a stimulus to initiate expression. In the case of inducible expression, protein production can be initiated when desired by, for example, addition of an inducer substance to the culture medium, for example, isopropyl □-D-1-thiogalactopyranoside (IPTG) or methanol. Polypeptide can be recovered and purified from host cells by a number of techniques known in the art, for example, chromatography e.g., HPLC or affinity columns.

In some embodiments, the peptide of the present invention can be said to be "isolated" or "purified" if it is substantially free of cellular material or chemical precursors or other chemicals that may be involved in the process of peptide preparation. It is understood that the term "isolated" or "purified" does not necessarily reflect the extent to which the peptide has been "absolutely" isolated or purified e.g. by removing all other substances (e.g., impurities or cellular components). In some cases, for example, an isolated or purified peptide includes a preparation containing the peptide having less than 50%, 40%, 30%, 20% or 10% (by weight) of other proteins (e.g. cellular proteins), having less than 50%, 40%, 30%, 20% or 10% (by volume) of culture medium, or having less than 50%, 40%, 30%, 20% or 10% (by weight) of chemical precursors or other chemicals involved in synthesis procedures.

In use, the defense signaling peptide of the invention can be admixed with an agriculturally acceptable carrier to form an agricultural composition which is to be applied to plants in need. Examples of the agriculturally acceptable carrier as used in the invention include but are not limited to water, alcohols, mineral or vegetable oils, calcium carbonate, talc, powdered magnesia, gypsum, and diatomaceous earth. The agricultural composition may be in the form of emulsions, liquids, oils, water soluble powders, wettable powders, flowables, powders, subtilized granules, granules, aerosols, fumigants, pastes and the like.

According to the present invention, the defense signaling peptide of the invention or a composition comprising the same can be applied to a plant to increase plant defense activity. It is effective in inducing systemic immune responses so as to increase resistance against biological threats.

Specifically, the plant applied with the defense signaling peptide of the invention or a composition comprising the same exhibit increased defense activity, as compared to a control plant without application of the defense signaling peptide of the invention or a composition comprising the same.

In certain embodiments, the defense activity as described herein includes production of hydrogen peroxide ($H_2O_2$), generation of a plant hormone, e.g. jasmonate (JA), JA conjugated with amino acid isoleucine (JA-Ile) or salicylic acid (SA), or expression of an anti-herbivore or anti-pathogen protein, e.g. proteinase inhibitor 1 (PI-1), proteinase inhibitor 2 (PI-2), pathogenesis-related protein 1b (PR-1b, cape1 precursor gene), beta-1,3-glucanase (PR-2), cys protease (PR-7), class ii chitinase (Chi2; 1), ethylene response factor 5 (ERF5) or avrpto-dependent pto-interacting protein 3 (Adi3). See FIG. 3.

In particular, the present invention is useful in increasing a plant's resistance to a wide variety of pathogens, including but not limited to, bacteria, insects, nematodes, fungi and the like.

Figure 4:
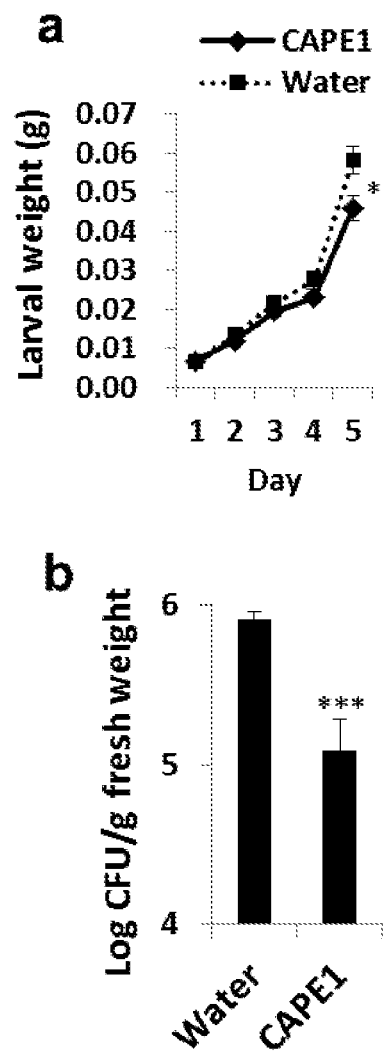

In certain embodiments, insect larvae fed with plant leaves pre-treated with a defense signaling peptide of the invention exhibit a reduced size by about 20%, as compared with control insect larvae fed with plant leaves pre-treated with water. See FIG. 4 (a).

In certain embodiments, a plant pre-sprayed with a defense signaling peptide of the invention exhibits reduced infection symptoms and decreased bacterial numbers per fresh weight, after bacterial inoculation, as compared with a control plant without application of the defense signaling peptide of the invention. See FIG. 4(b).

The defense signaling peptide of the invention is applicable to a verity of plant species. Plants to which the inventive method can be applied include both monocotyledon and dicotyledon. Examples of monocotyledon includes but not limited to rice, barley, wheat, rye, oat, corn, bamboo, sugar cane, onion, leek and ginger. Examples of the dicotyledons include, but are not limited to *Arabidopsis thaliana*, eggplant, tobacco plant, red pepper, tomato, burdock, crown daisy, lettuce, balloon flower, spinach, chard, potato, celery, carrot, water dropwort, parsley, Chinese cabbage, cabbage, radish, watermelon, melon, cucumber, pumpkin, gourd, strawberry, soybean, mung bean, kidney bean, and pea.

In some embodiments, a defense signaling peptide as described herein is included in a composition at a concentration of about 50 nM or more, 100 nM or more, 150 nM or more, 200 nM or more or 250 nM or more.

In some embodiments, a composition comprising a defense signaling peptide as described herein is sprayed to a plant in need for 1 min or more and the defense response can be induced within 2 hours and last more than 24 hours.

Accordingly, the method of the invention for treating a plant to increase plant defense activity by using a defense signaling peptide as described herein provides a variety of advantages, at least including (1) it is effective in inducing systemic immune responses in plants against numerous biological threats; (2) it is performed by simply applying the defense signaling peptide of the invention to a plant in need, (3) a low dose of the defense signaling peptide of the invention is sufficient; (4) the defense signaling peptide of the invention is short in length and can be easily made by chemical synthesis; and (5) no transgenic technology or agrichemicals is needed which may cause environmental problems.

In some embodiments, an overly strong defense activity in plants is not preferred due to decreased growth. Therefore, proper regulation of a defense activity is desired. In the present invention, it is found that the CNYx (SEQ ID NO: 55) is a core structure for designing protease inhibitor to prevent processing and decrease defense activity. Therefore, a peptide having the CNYx motif (SEQ ID NO: 55) but lacking the active PxGNxxxxxPY motif (SEQ ID NO: 1) to provide a define activity can be used as a protease inhibitor/competitor to reduce or block activity of the endogenous protease in cleaving the precursor peptide to generate the active defense signaling peptide of PxGNxxxxxPY (SEQ ID NO: 1) and thus to regulate the defense activity in plants.

Accordingly, the present invention relates to a method of down regulating a defense activity in a plant, comprising treating the plant with a peptide having a CNYx motif (SEQ ID NO: 54) but lacking a 11-amino acid signaling peptide motif (PxGNxxxxxPY) (SEQ ID NO: 1) in an amount to effectively reduce or block the enzymatic activity in cleaving a precursor peptide (e.g. CNYxPxGNxxxxxPY (SEQ ID NO: 15) or the full length of PR-1) to generate a plant defense signaling peptide of PxGNxxxxxPY (SEQ ID NO: 1) as described above.

In some embodiments, a peptide as a protease inhibitor according to the present invention preferably has up to about 50 amino acid residues or 40, or 30, or 20, 15 or 10 amino acid residues, for example, at least 4 amino acid residues, particularly 5, 6, 7, 8, 9 or 10 amino acid residues. In a specific example, a peptide as a protease inhibitor according to the present invention is SEQ ID NO: 55 (CNYDPV).

The present invention is further illustrated by the following examples, which are provided for the purpose of demonstration rather than limitation. Those of skill in the art should, in light of the present disclosure, appreciate that many changes can be made in the specific embodiments which are disclosed and still obtain a like or similar result without departing from the spirit and scope of the invention.

Examples

Many important intercellular communication events in multicellular organisms are mediated by peptides, but only a few peptides have been identified in plants. In an attempt to address the difficulties in identifying plant signaling peptides, we developed a novel peptidomics approach and used this approach to discover defense signaling peptides in plants. In addition to the canonical peptide systemin, several novel peptides were confidently identified in *Solanum lycopersicum* (tomato) and quantified to be both wounding- and MeJA-induced. A wounding or wounding plus MeJA-induced peptide derived from the pathogenesis-related protein 1 (PR-1) family was found to induce significant anti-pathogen and minor anti-herbivore responses in tomato. This study highlights a role for PR-1 in immune signaling and suggests the potential application of plant endogenous peptides in efforts to defeat biological threats in crop production. As PR-1 is highly conserved across many organisms and the putative peptide from At-PR1 was also found to be bioactive in *Arabidopsis*, our results suggest that this peptide may be useful for enhancing resistance to stress in other plant species.

1. Material and Methods 1.1 Chemicals, Enzymes and Materials

Tris (2-carboxyethyl) phosphine hydrochloride (TCEP), methyl methanethiosulfonate (MMTS), 3,3-diaminobenzidine (DAB), potassium hydroxide (KOH), sodium hydroxide (NaOH), hydrogen chloride (HCl), 10× Murashige and Skoog (MS) basal salt micronutrient mixture, King Agar B medium, isopropanol, ethanol, chloroform, methyl jasmonate (MeJA, 95% solution), Triton X-100, β-casein, salicylic acid (SA), 2-hydroxybenzoic acid-[$^2$H$_6$] (d$_6$-SA) and jasmonic acid (JA) were purchased from Sigma-Aldrich (St. Louis, Mo.). Dihydrojasmonic acid (H$_2$JA) was purchased from OlChemim (Olomouc, Czech Republic). Analytical grade methanol, acetonitrile (ACN) and trifluoroacetic acid (TFA) were purchased from Merck (Darmstadt, Germany). LC-MS grade ACN with 0.1% formic acid (FA) was from J. T. Baker (Phillipsburg, N.J.). Deionized water (18.1 MΩ·cm resistivity) from Milli-Q system (Millipore, Bedford, Mass.) was used throughout this work. C18 Zip Tip and Millex HA 0.45 μm filters were purchased from Millipore (Billerica, Mass.). The TriPure RNA Isolation Reagent and FastStart Universal SYBR Green Master (ROX) Kit were purchased from Roche (Indianapolis, Ind.). The RNA purification reagent RNAmate was from BioChain (Hayward, Calif.). The SuperScript III Reverse Transcriptase Kit was purchased from Invitrogen (Carlsbad, Calif.). Fast-Run HotStart PCR Mix was from Postech (Taipei, Taiwan). Miracloth was purchased from Calbiochem (La Jolla, Calif.). The customized Sep-Pak C18 Cartridge 60 cc (20 g) was purchased from Waters (Wexford, Ireland). Gel filtration XK 16/40 column and packing gel (Sephadex G-25 Fine) were purchased from GE Healthcare Bio-Sciences AB (Uppsala, Sweden). Tryptic enolase and [Glu1]-Fibrinopeptide (GFP) was purchased from Waters (Milford, Mass.). Trypsin (modified, sequencing grade) was purchased from Promega (Madison, Wis.). Systemin (AVQSKPPSKRDPPKMQTD, SEQ ID NO: 58), CAPE1 (PVGNWIGQRPY, SEQ ID NO: 2), AtCAPE1 (PAGNYIGARPY, SEQ ID NO:

19) AtCAPE9 (PRGNYVNEKPY, SEQ ID NO: 27), cleavage motif (CNYDPV, SEQ ID NO: 56) and internal standard (PAAAYIGARAY, SEQ ID NO: 59) were synthesized and purified to >95% purity by Yao-Hong Biotechnology (Taipei, Taiwan). The flg22 (QRLSTGSRINSAKD-DAAGLQIA, SEQ ID NO: 60) with purity >95% purity was purchased from KareBay Biochem, Inc. (Monmouth Junction, N.J.). The purity of synthetic peptide was further checked to over 95% using nanoUHPLC-MS.

1.2 Plant Materials and Growth Conditions

Tomato (*Solanum lycopersicum* cv. CL5915) seeds were provided by AVRDC—The World Vegetable Center (Tainan, Taiwan). The tomato plants were kept at 25° C. day/20° C. night temperature under a 12 hour light/12 hour dark photoperiod. Tomato seeds were germinated in soil and grown in a growth chamber for 2 weeks. For detection of endogenous peptides, the 2-week-old plants were transferred and maintained in a phytotron for 6 weeks. The tomato plants for peptide treatments were continuously grown in a growth chamber for 5 weeks. To examine the peptide activity in *Arabidopsis*, *Arabidopsis thaliana* (ecotype Columbia) seeds were germinated in soil and grown in a growth chamber at 22° C. day/20° C. night temperature under a 8 hour light/16 hour dark photoperiod for 4 weeks. For salt treatment, Seeds were surface sterilized with 30% bleach (CLOROX) for 8 min and then washed with sterilized ddH2O five times. Seeds were germinated on half-strength Murashige and Skoog (½ MS) medium under a 16 h photoperiod (80-100 μmol m⁻2 s⁻1 illumination) at 22° C.

1.3 Plant Treatments

To extract the wound-induced peptides, the tomato plants were mechanically wounded by cutting across the surface of the mesophyll with a pair of scissors and spraying with 1.25 mM MeJA in 0.1% Triton X-100 solution for 15 hours (Pearce et al., 2001a). For direct quantitation of CAPE1 in tomato, unwounded, wounded, or wounded plus MeJA treated plants for 15 hours were used to study peptide induction. To examine the possible function of peptide using cDNA microarray analysis, detached tomato leaves were immersed in water or 250 nM CAPE1 in aqueous solution for 1, 2, 4, and 8 hours, respectively. To confirm the gene expression induced by the peptide, the tomato plants were collected after spraying with 250 nM CAPE1 or water for 0, 4, 8 and 24 hours. To compare the ROS induced by different treatments, detached tomato leaves were treated with water (control), mechanical wounding (MW), 1.25 mM MeJA, 250 nM systemin or 250 nM CAPE1 for 4 hours. To test the anti-herbivore activity induced by the peptide, the tomato plants were collected after spraying with 250 nM CAPE1 or water for 24 hours before feeding with insects. To compare the PI genes induced by the peptides, detached tomato leaves were immersed in 250 nM CAPE1, 250 nM systemin or water for 1, 2, and 4 hours. To compare the jasmonates induced by the peptides, the excised tomato plants were treated with 10 mM phosphate buffer, 365 nM systemin or 365 nM CAPE1 in buffer through the cut stem for 2 and 4 hours (Schaller et al., 1995; Howe et al., 1996). To compare the salicylic acid induced by peptides, the tomato plants were treated with 10 mM phosphate buffer, 365 nM flg22 or 365 nM CAPE1 in buffer through the cut stems of excised plants for 8 hours. To compare the WRKY53 and PR-1b genes induced by the peptides, detached tomato leaves were immersed in 250 nM CAPE1, 250 nM flg22 or water for 2 hours. To test the anti-pathogen activity induced by peptides, three groups of the tomato plants were sprayed with 100 nM CAPE1, 100 nM flg22, or water, respectively, for 2 hours prior to pathogen challenge. To test the anti-pathogen activity induced by peptides in *Arabidopsis*, the plants were sprayed with 100 nM AtCAPE1, AtCAPE9, 100 nM flg22 or water, respectively, for 2 hours prior to pathogen challenge. *Arabidopsis* seedlings treated with 50 mM NaCl for 24 h with or W/O 250 nM AtCAPE1 or AtCAPE9 for 6 h after salt treatment. To test cleavage motif can be a protease inhibitor, the tomato plants were sprayed with 1 μM CNYDPV for 2 hours prior to pathogen challenge.

1.4 Endogenous Peptide Extraction in Tomato and *Arabidopsis*

The unwounded and wounding plus MeJA treated tomato leaves were collected and individually ground into powder under liquid nitrogen by a blender (Waring Commercial, New Hartford, N.Y.). Frozen leaf powder (150 g) was dissolved in 200 ml of 1% TFA and homogenized to leaf juice by a blender for 2 minutes. The leaf juice was filtered through four layers of cheesecloth and one layer of Miracloth. The filtrated leaf juice was then centrifuged at 10,000×g for 20 minutes at 4° C. The supernatant was adjusted to pH 4.5 with 10 N NaOH and centrifuged at 10,000×g for 20 minutes at 4° C. Then the supernatant was re-adjusted to pH 2.5 using TFA and 150 μg tryptic β-casein peptides were added to the supernatant as an internal control for peptide quantity before purification. To avoid the trypsin residue reacting with the endogenous proteins or peptides, the tryptic β-casein peptides were acidified by TFA and purified using C18 Zip Tip. Before purifying the supernatant using a Sep-Pak cartridge, the stationary phase was first equilibrated by 60 ml 0.1% TFA. The supernatant was loaded into the Sep-Pak cartridge, washed with 120 ml 0.1% TFA and eluted by 200 ml of 60% methanol in 0.1% TFA. The eluted solution was vacuum-evaporated to remove methanol using a vacuum centrifugation concentrator (miVac Duo Concentrator, Genevac, Gardiner, N.Y.) first and then using a lyophilizer (EYELA, Miyagi, Japan) to dryness (Pearce et al., 1991). To profile total endogenous peptides using LC-MS operated in data dependent acquisition (DDA) mode, the lyophilized crude extract was dissolved in 1 ml of 0.1% TFA, centrifuged at 10,000×g for 10 minutes at 4° C. and filtered through a Millex HA 0.45 nm filter before peptide fractionation. For the peptide fractionation, the filtrated peptide extract was injected into a Sephadex G-25 column and eluted by 1 ml/min of 0.1% TFA with 1 fraction/min collection. Ten fractions from elution times of 22-31 minutes were collected and evaporated to dryness using a vacuum centrifugation concentrator. Each fraction was purified by $C_{18}$ Zip Tip for LC-MS/MS analysis. For targeted peptide analysis using LC-MS operated in selected reaction monitoring (SRM) mode, the endogenous peptides were extracted from the unwounded, wounding only and wounding plus MeJA treated tomato leaves using the same procedure but without gel-filtration fractionation. Ten-day-old *Arabidopsis* seedlings grown vertically on ½ MS medium were transferred to a hydroponic system culture of ½ MS liquid medium without sucrose. The medium was changed every 4 days. Three weeks after planting, the plant tissue was harvested. For salt treatments, fresh ½ MS medium in the presence or absence of 125 mM NaCl was exchanged and the treatments were prolonged to 24 h. Samples were homogenized with 200 ml of 1% (v/v) chilled trifluoroacetic acid (TFA; Sigma-Aldrich) in a blender for 2 min. To normalize the variations in sample preparation and for better quantification accuracy by liquid chromatography-tandem mass spectrometry (LC-MS/MS) analysis, 20 μl of 1 pmole μl-1 of internal standard (synthetic peptide: PAAAYIGARAY, SEQ ID NO: 59) with two amino acid substitutions of G3A and N4A of AtCAPE1 was added to the extraction buffer while crude peptide was isolated. The extracts were then filtered through four layers of Miracloth (Calbiochem, San Diego, Calif., USA) to remove plant debris. The procedure followed a previously described protocol (Pearce et al., 2001a, b). After centrifuging at 8500 rpm for 20 min at 4° C. (Beckman Coulter, Avanti J-26 XP), the pH value of the supernatant was adjusted to 4.5. The extracts were then centrifuged again at 8500 rpm for 20 min at 4° C. and the pH value of supernatant was adjusted to 2.5. Subsequently, the supernatant was bound with a customized Sep-Pak C18 solid phase extraction cartridge (Waters, Milford, Mass., USA) according to the following steps: the C18 cartridge was conditioned by 0.1% (v/v) TFA first, bound with the supernatant, and then washed with 0.1% (v/v) TFA. Finally, the polypeptides were eluted with 60% (v/v) methanol/0.1% (v/v) TFA. The peptides in the final eluate were evaporated to dryness by rotary evaporation under high vacuum, and the pellets were resuspended in 0.1% (v/v) TFA. The polypeptides were further fractionated by fast protein liquid chromatography (ÄKTA purifier) to remove protein contaminates with size exclusion columns (Superdex peptide 10/300 GL; GE Healthcare, Little Chalfont, UK). Fractions containing polypeptides or small proteins with similar sizes to AtCAPE1 were collected and combined. The combined eluates were rotary evaporated under high vacuum and resuspended in 0.1% (v/v) TFA for ZipTip (Millipore, Billerica, Mass., USA) to remove the contamination of salts. After final evaporation and resuspension in 0.1% (v/v) formic acid (Fluka), targeted LC-MS/MS analysis was performed. Targeted LC-MS/MS analysis.

1.5 Endogenous Peptide Profiling Using LC-MS/MS

For endogenous peptide profiling, LC-MS/MS analysis was performed with a nanoUHPLC system (nanoACQUITY UPLC, Waters, Millford, Mass.) coupled online to the nano-electrospray source of a hybrid quadruple time-of-flight mass spectrometer (SYNAPT HDMS G1, Waters, Manchester, UK). The SYNAPT HDMS G1 instrument was operated in the positive ion mode and DDA methods for detection of endogenous peptides. The sample was loaded into a 180 μm×50 mm tunnel frit trap column packed with 20 mm of 5 μm Symmetry C18 particles (Waters, Millford, Mass.) and separated online with a 75 μm×250 mm tunnel frit analytical column packed with 250 mm of 1.7 μm BEH C18 particles (Waters, Millford, Mass.) using a 95 minute gradient flow with 300 nl/min and 5-90% ACN/0.1% FA ratio (Chen et al., 2012). The DDA acquisition parameters were set to one full MS scan (m/z 400-1600) with a scan time of 0.6 seconds and switched to three product ion scans (m/z 100-1990) with a scan time of 1.2 seconds when a precursor ion charge was 2+, 3+ and 4+ and an intensity greater than 20 counts was detected. The data generated from SYNAPT HDMS G1 were first converted into mzXML format (Pedrioli et al., 2004) using massWolf (version 4.3.1) and then processed by UniQua with default parameters for SYNAPT HDMS G1 (Chang et al., 2013). The UniQua processed spectra were converted into Mascot generic format (.mgf) using mzXML2Search from Trans Proteomics Pipeline (TPP) version 4.4 rev. 1 (Pedrioli, 2010). For detection of *Arabidopsis* CAPE1, an LTQ Velos PRO mass spectrometer (Thermo Scientific, Waltham, Mass., USA) coupled with an online capillary nanoUHPLC system (Waters) was utilized for peptide identification and quantification. The capillary LC system was equipped with a homemade C18 trap cartridge (5 μm particles, Symmetry C18; Waters), and a homemade C18 reversed-phase analytical column (1.7 μm particles, BEH130 C18; Waters) (Chen et al., 2012) was used to deliver the solvent and target peptide with a linear gradient from 8 to 90% (v/v) acetonitrile in 0.1% (v/v) formic acid for 95 min at a nanoflow rate (approx. 300 nl min-1). The analytical column was coupled to a nanoelectrospray ionization source, and acquisition of the data was performed with a full MS scan followed by MS/MS scans of the targeted precursor ions. Precursor ions of AtCAPE1 (PAGNYIGARPY (SEQ ID NO: 19); m/z 589.8) and the internal standard (PAAAYIGARAY (SEQ ID NO: 59); m/z 562.4) were selected for subsequent targeted MS/MS scans. The fragment ions m/z 563.2, 676.3, and 900.5 and m/z 537.2, 650.3, and 813.34 were used for further identification and quantification of AtCAPE1 and the internal standard, respectively.

1.6 Hypothetical and Decoy Database

The tomato hypothetical peptide database (TomHT database) was composed by extracting 50 residues of all protein C-terminal sequences from the International Tomato Annotation Group (ITAG) protein database (release version 2.3, total protein entries=34,728) with the addition of the bovine β-casein sequence. The randomized databases (Ran Databases) were generated by shuffling sequences in the target databases using Perl script (decoy.pl) provided by Matrix Science (London, UK).

1.7 Endogenous Peptide Identification and Quantitation

The processed mgf files were searched against the TomHT database without specifying enzyme cleavage rules using a Mascot MS/MS ion search (Matrix Science, server version 2.3). The mass tolerance in the MS/MS ion search for peptide precursors and fragments was ±0.1 Da. The Mascot search results from the randomized database were used to evaluate the score to cutoff the random matched peptides.

1.8 Phytohormone Extraction

After peptide treatment, the metabolites were extracted from leaf tissues for phytohormone quantitation. The extraction procedure was modified from a previously published protocol (Pan et al., 2010). The leaf tissues (about 0.6 g fresh weight) were ground into powder under liquid nitrogen and transferred to a 50 ml screw-cap tube. The frozen leaf powder was dissolved in 6 ml extraction solvent and d6-SA (3 ng to 0.6 g leaf tissue) and $H_2JA$ (15 ng to 0.6 g leaf tissue) were added as internal standards. The samples were extracted by shaking at a speed of 100 rpm at 4° C. for 30 minutes and then 12 ml dichloromethane was added to each sample and shaken at 100 rpm at 4° C. for 30 minutes. The samples were centrifuged at 13,000×g at 4° C. for 5 minutes, and two phases were formed. The lower phase was transferred carefully into a new tube and evaporated to dryness by a vacuum centrifugal concentrator for about 1 hour. The dried samples were dissolved in 300 μl methanol, mixed well and centrifuged at 10,000×g at 4° C. for 5 minutes and then the supernatant was transferred to the sample vial for targeted quantitation analysis using LC-MS/MS.

1.9 Targeted Peptide and Phytohormone Quantitation Using LC-MS/MS

For targeted peptide quantitation, the nanoUHPLC method was the same as for endogenous peptide profiling and the MS (LTQ Velos Pro, Thermo Fisher Scientific, San Jose, Calif.) was set to one full MS scan (m/z 400-1600) with enhanced scan speed and switched to one selected reaction monitoring (SRM) scan with normal scan speed. For SRM targeted on CAPE1, the doubly charged CAPE1 precursor ion m/z was selected (m/z 643.84) for fragmentation and product ions m/z of 620.34, 733.37 and 1090.57 were monitored. The relative abundances of CAPE1 in wounded and unwounded samples were estimated by combining SRM peak areas of product ions.

For phytohormone quantitation, a linear ion trap-orbitrap mass spectrometer (Orbitrap Elite, Thermo Fisher Scientific, Bremen, Germany) coupled online with a UHPLC system (ACQUITY UPLC, Waters, Millford, Mass.) was used. The phytohormones were separated by a HSS T3 column (Waters, Millford, Mass.) using gradients of 0.5-25% ACN at 0-2 min, 25-75% ACN at 2-7 minutes and 75-9.5% ACN at 7-7.5 minutes. The mass spectrometer was operated in the negative ion mode and set to one full FT-MS scan (m/z 100-600) with 60,000 resolution and switched to five FT-MS product ion scans (in 30,000 resolution) for five precursors: m/z of 137.02 (for SA), 209.12 (for JA), 322.20 (for JA-Ile), 141.05 (for $d_6$-SA dissociated to $d_4$-SA) and 211.13 (for $H_2JA$). The fragmentation reactions of m/z 137.02 to 93.03 for SA, 209.12 to 59.01 for JA, 322.20 to 130.09 for JA-Ile, 141.05 to 97.06 for $d_6$-SA and 211.13 to 59.01 for $H_2JA$ were selected for quantitation. The absolute abundances of JA, JA-Ile and SA were calculated by the abundance of $d_6$-SA and $H_2JA$.

1.10 Quantitative Real Time PCR (qRT-PCR)

Quantitative real-time PCR (qRT-PCR) was used to validate the expression of some specific genes. Three biological replicates were used for qRT-PCR analyses. The qRT-PCR was performed using SYBR Green reagent and ABI 7500 Real Time PCR systems (Foster City, Calif.). The PCR cycling steps were 50° C. for 2 min and 94° C. for 10 min for initial steps and followed by 95° C. for 15 s and 60° C. for 1 min for 40 cycles. The gene expressions across different samples were normalized with internal control EF-1α or Ubi3. The primers used are listed in Table 3. The melting curve was used to verify the specificity of the PCR product.

TABLE 3 primers for qRT-PCR.

| Gene | Gene Accession # | Primer (5'→3') | Product size (bp) |
|---|---|---|---|
| Elongation Factor 1a (EF-1a) | X14449 | For: CTCCGTCTTCCACTTCAGG (SEQ ID NO: 63) Rev: TCAGTTGTCAAACCAGTAGGG (SEQ ID NO: 64) | 128 |
| Ubiquitin 3 (Ubi3) | X58523 | For: ACTCTTGCCGACTACAACATCC (SEQ ID NO: 65) Rev: CTCCTTACGAAGCCTCTGAACC (SEQ ID NO: 66) | 198 |
| Proteinase Inhibitor 1 (PI-1) | K03290 | For: CTTCTTCCAACTTCCTTTG (SEQ ID NO: 67) Rev: TGTTTTCCTTCGCACATC (SEQ ID NO: 68) | 110 |
| Proteinase Inhibitor 2 (PI-2) | K03291 | For: AATTATCCATCATGGCTGTTCAC (SEQ ID NO: 69) Rev: CCTTTTTGGATCAGATTCTCCTT (SEQ ID NO: 70) | 254 |
| AvrPto-dependent Pto-interacting protein 3 (Adi3) | NM_001247682 | For: AGGCAGTTTCCTATAGGGCTA (SEQ ID NO: 71) Rev: TCGACCATCAGGTCTTCTTCC (SEQ ID NO: 72) | 155 |
| Ethylene response factor 5 (ERF5) | NM_001247583 | For: ATGGGTTCTCCACAAGAGAC (SEQ ID NO: 73) Rev: GAAGCTTGCGATGTCATCAA (SEQ ID NO: 74) | 132 |
| Pathogenesis-related protein 1b (PR-1b) | M69248.1 | For: CTCATATGAGACGTCGAGAAG (SEQ ID NO: 75) Rev: GGAAACAAGAAGATGCAGTACTTAA (SEQ ID NO: 76) | 204 |
| beta-1,3-glucanase (PR-2) | NM_001247869.1 | For: CAAATAACAGGAGCGCAGCC (SEQ ID NO: 77) Rev: GTTACTTCCTTTGAGGGCAT (SEQ ID NO: 78) | 163 |
| Cys protease (PR-7) | CK574973.1 | For: TCAGCACCTCTGGACCTTT (SEQ ID NO: 79) Rev: GCTCCTGAAGGCTCTGTTA (SEQ ID NO: 80) | 141 |
| Class II chitinase (Chi;2) | U30465.1 | For: TTTTGGTCGAGGTCCTATCC (SEQ ID NO: 81) Rev: GTAATGACATCGTGTGCCGA (SEQ ID NO: 82) | 186 |
| WRKY transcription factor 53 (WRKY53) | Solyc08g008280.2.1 | For: AAATGGATTGTGCATCAAACTGGGA (SEQ ID NO: 83) Rev: AGCCACCCCAGTTGAGAATCAACA (SEQ ID NO: 84) | 189 |

1.11 In Vivo Detection of $H_2O_2$

The 3,3-diaminobenzidine (DAB) was dissolved with 1 N HCl and adjusted to pH 3.8 with NaOH to a final concentration of 1 mg/ml. After plant treatments, the detached leaves were continuously supplied with DAB solutions for 8 hours in the dark and then decolorized by boiling ethanol (96%) for 10 minutes. The leaves were cooled to room temperature and preserved in fresh ethanol.

1.12 Herbivory Treatments

The *Spodoptera litura* larval eggs were originally obtained from Taiwan Agricultural Chemicals and Toxic Substances Research Institute (Taichung County, Taiwan). Thirty uniformly sized larvae of the first instar stage were used for the anti-insect bioassay study. The larvae were continuously fed with tomato leaves harvested from water or CAPE1 presprayed plants every 24 hours for 5 days. All larval weights were recorded for each day and the averages of larval weights were calculated. The larval sizes were observed after 5 days of feeding.

1.13 Pathogen Growth and Challenge

The bacterial pathogen *Pseudomonas syringae* pv. tomato DC3000 (Pst DC3000) or Pst DC3000 hrcC$^-$ were grown on King's B (KB) agar medium containing 100 mg/L rifampicin for 2 days at 28° C. Before the challenge, the bacteria were cultured in KB liquid medium at 28° C. with 230 rpm shaking overnight. The bacteria were pelleted by centrifugation and resuspended in 10 mM $MgSO_4$ at $A600=0.25$ (about $10^8$ cfu/ml). The plants were dipped into a diluted suspension of $10^5$ cfu/ml Pst DC3000 in 10 mM $MgSO_4$ containing 0.005% Silwet L-77 under vacuum for 30 seconds. Pst DC3000 or hrcC$^-$ were grown in water- or peptide-treated plants for several days to observe the symptoms and then the bacteria were collected from the leaves and evaluated by bacterial titers according to a method outlined previously (Zimmerli et al., 2000).

1.14 Western Blot Analysis

Ten-day-old CAPE1oxCNYD or CAPE1oxCNAD seedlings were subjected to medium supplemented with or without different NaCl concentration and with or without 125 mM NaCl for various time points. The collected samples were crushed with YSZ Grinding Media (EE-TEC, EZEAG0500) in 2 mL eppendorf tubes by sonication (KURABO, SH-48). During the preparation, the samples were submerged in liquid nitrogen for rapid freezing. The samples were then homogenized in extraction buffer (50 mM Tris-HCl, pH 7.5, 150 mM NaCl, 20 mM EDTA, 1% [w/v] SDS and 10% [v/v] glycerol) at 95° C. for 5 mM. After centrifuging at 12,000 rpm for 10 mM, the supernatant was transferred to a new eppendorf tube. Fifty micrograms of total proteins were loaded on 10% SDS-polyacrylamide gels and analyzed by western blotting. The recombinant PROAt-CAPE1 tagged eYFP was detected by anti-GFP antibody (Roche; 11814460001), and horseradish peroxidase-conjugated anti-mouse antibody (Invitrogen; 616520) was used as a secondary antibody. To confirm the equal loading of total proteins, an anti-α-tubulin antibody (Sigma-Aldrich; T5168) was subsequently used to probe the same blot.

1.15 Accession Numbers

Sequence data from this article can be found in the International Tomato Annotation Group (ITAG) protein database or Genbank/EMBL databases. Sequence data of putative CAPE peptides in *Arabidopsis* from this article can be found in the *Arabidopsis* Genome Initiative under the following accession numbers: AT4G33730.1, AT4G25780.1, AT4G33720.1, AT4G25790.1, AT5G57625.1, AT4G30320.1, AT2G14580.1 (PRB1), AT5G26130.1 and AT2G14610.1 (PR1).

2. Results

2.1 Identification of Wounding-Plus MeJA-Induced Peptides in Tomato Leaves

Quantitative analysis revealed a novel peptides and a known peptide (systemin) which showed no significant expression in the unwounded plant but was highly expressed after wounding plus MeJA treatment. The novel peptide derived from pathogenesis-related protein 1b (PR-1b) showed a similar expression response to systemin. Since PR-1b is classified as a member of the cysteine-rich secretory proteins, antigen 5, and pathogenesis-related 1 proteins (CAP) superfamily (Gibbs et al., 2008), this peptide was designated as CAP-derived peptide 1 (CAPE1). In CAPE1 identification, with the exception of the y1 and b1 ions, most of the y and b fragment ions were matched to the theoretical fragments of the CAPE1 sequence. Using this approach, the tissue quantity used for global peptide identification was <150 g. To confirm the matched sequences, synthetic CAPE1 was analyzed by MS/MS and the resulting spectrum was totally matched to the endogenous CAPE1. Without peptide pre-fractionation, total peptides extracted from the unwounded, mechanically wounded and wounded plus MeJA treated tomato plants were directly analyzed by nanoUHPLC-SRM-MS targeted on the specific CAPE1 collisional induced dissociation (CID) reaction. The quantitation result showed that CAPE1 was expressed in low level in unwounded plants but significantly induced after wounding or wounding plus MeJA treatments (FIG. 1).

2.2 Bioactivity of CAPE1

Figure 2:
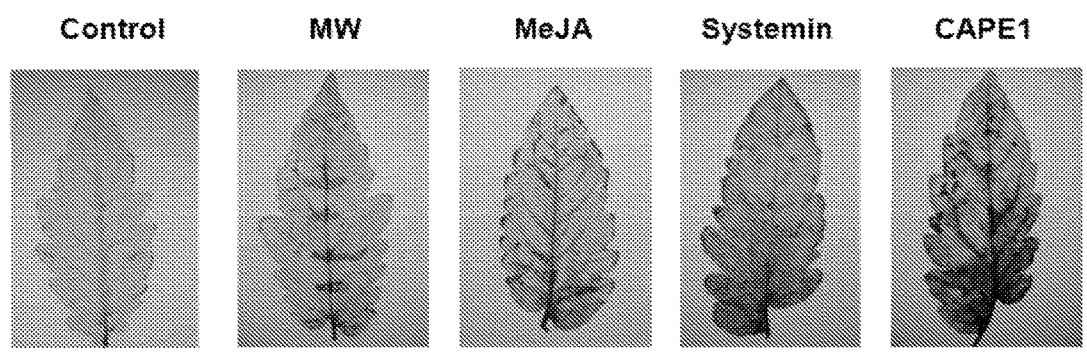
Figure 3:
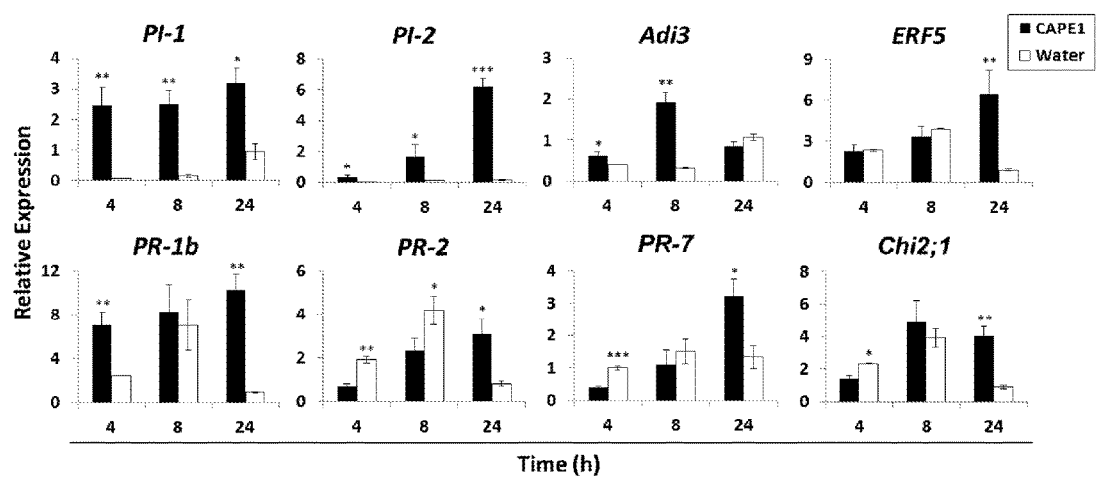

CAPE1 treatment induces $H_2O_2$ formation in tomato leaves as detected by DAB staining (FIG. 2). The profiles of induced genes obtained by microarray analysis suggest that CAPE1 elevates the expression of several genes known to be involved in the anti-herbivore and anti-pathogen defense response. CAPE1 mainly induced genes involved in the stress response, defense response, innate immune response, bacterial defense and systemic acquired resistance (SAR). Reverse transcription quantitative PCR (qRT-PCR) analysis further confirmed that the anti-herbivore genes PROTEINASE INHIBITOR 1 and 2 (PI-1 and PI-2) and pathogen-related genes PATHOGENESIS-RELATED PROTEIN 1b (PR-1b, CAPE1 precursor gene), BETA-1,3-GLUCANASE (PR-2), CYS PROTEASE (PR-7), CLASS II CHITINASE (Chi2; 1), ETHYLENE RESPONSE FACTOR 5 (ERF5) and AvrPto-DEPENDENT Pto-INTERACTING PROTEIN 3 (Adi3) were activated after CAPE1 treatment (FIG. 3).

The anti-herbivore response was evaluated by average larval weights of 30 *Spodoptera litura* larvae fed with tomato leaves pretreated with water or CAPE1. Tomato plants pre-sprayed with CAPE1 suppressed larval growth and reduced larval weight by about 20% (FIG. 4a). To demonstrate that plant resistance can also be enhanced by CAPE1, two groups of tomato plants were pre-sprayed with water or synthetic CAPE1 for 2 hours. After the treatment, the two plant groups underwent challenge with the pathogen *Pseudomonas syringae* pv. tomato DC3000 (Pst DC3000). As shown in FIG. 4b, the water pretreated tomato plants showed severe pathogen infection symptoms.

Figure 5:
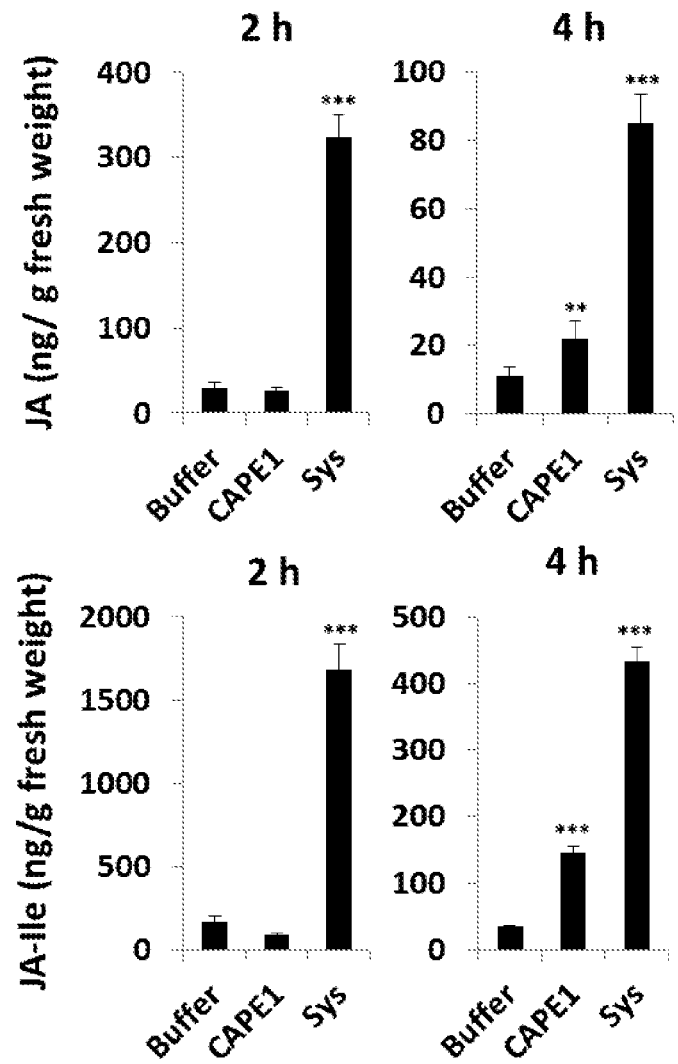
Figure 6:
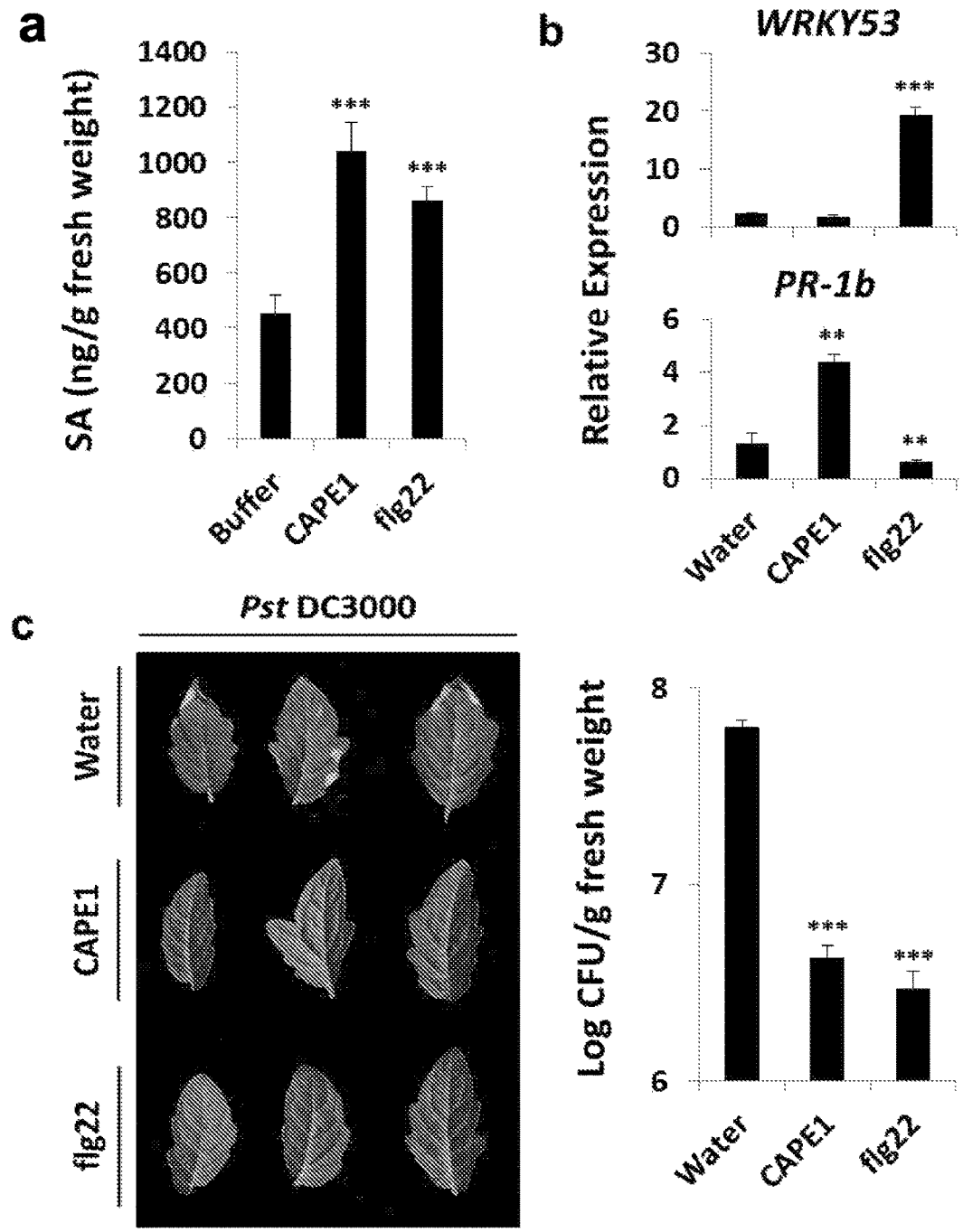

To compare the anti-herbivore response of systemin with CAPE1, excised tomato plants were used, since the excised plant treated with peptide solution has been used previously to test the bioactivity of systemin (Schaller et al., 1995; Howe et al., 1996). JA and JA-Ile were observed to be significantly induced by treatment for 2 hours with systemin, but was induced after 4 hours treatment with CAPE1, and the expression level was ~4 fold lower than that of systemin (FIG. 5). As the results suggested that CAPE1 may be a novel DAMP signal for the induction of immunity to pathogenesis, next, CAPE1 was compared with the canonical Pathogen/Microbe Associated Molecular Pattern (PAMP/MAMP) peptide "flg22" (Hayashi et al., 2001). As shown in FIG. 6a, both CAPE1 and flg22 significantly induced SA when supplied to excised plants. In FIG. 6b, the flg22 highly induced WRKY TRANSCRIPTION FACTOR 53 (WRKY53) expression but not PR-1b in tomato. This result was consistent with the public RNA-seq data in the Tomato Functional Genomics Database (TFGD) (Fei et al., 2011), which are based on the experiment "transcriptome sequencing of tomato leaves treated with different bacteria and PAMPs" (Rosli et al., 2013). The RNA-seq data showed that WRKY53 could be induced but PR-1b, Adi3 and ERF5, but could not be significantly induced using 30 minute or 6 hours treatment of flg22 on the tomato. However, the CAPE1 did not induce WRKY53 but highly induced its precursor gene PR-1b. Spraying of plants for 2 hours with either CAPE1 or flg22 resulted in plant resistance to Pst DC3000 infection (FIG. 6c). The anti-pathogen responses including the SA biosynthesis and defense gene (ERF5 and PR-1b) expression can be induced by CAPE1 systemically. This data shows that the CAPE1 is a signaling peptide for regulating not only local but also systemic defense response throughout the whole plant (FIG. 7)

2.3 CAPE1 Proprotein

The mature CAPE1 peptide is derived from the C-terminal end of tomato PR-1b. This proprotein consists of an N-terminal signal peptide, a CAP domain and an extended C-terminal end (FIG. 8a). The phylogenetic analysis using Molecular Evolutionary Genetics Analysis version 5.2 (MEGA5.2)(Tamura et al., 2011) and C-terminal alignment of the PR-1b protein demonstrated that the full protein and extended C-terminal end are highly conserved across different flowering plants ranging from monocots to dicots (FIG. 8b). It is interesting that the PxGNxxxxxxPY-motif (SEQ ID NO: 1) was conserved in the CAPE1 sequence, and also that the three residue sequences before the cleavage site had a conserved CNYx motif (SEQ ID NO: 55) (FIG. 8c). This suggests that CNYx.PxGNxxxxxxPY- (SEQ ID NO: 28) could be a functional motif that may mark bioactive peptides in other species.

2.4 CAPE Peptides in *Arabidopsis*

To demonstrate that a peptide derived from the CNYx-.PxGNxxxxxxPY-motif (SEQ ID NO: 28) could be bioactive, the *Arabidopsis* CAPE homologs, AtCAPE1 and AtCAPE9 were selected. AtCAPE1 and AtCAPE9 have highest and lowest sequence identity compared with SolCAPE1. Both peptides were shown to increase immunity against Pst DC3000 infection (FIG. 9). To confirm this proteolytic process of the AtCAPE1 precursor, we generated a transgenic plant, CAPE1oxCNYD, where wild-type PROAtCAPE1 fused with C-terminal enhanced yellow fluorescent protein (eYFP) was constitutively overproduced by the 35S promoter. This data shows that the MWs of the two bands were close to that of the precursor protein tagged with eYFP (45.76 kDa) and the AtCAPE1 fused to eYFP (26.3 kDa), respectively, when the cleavage occurred at the predicted cleavage site (FIGS. 10a and 10b). In *Arabidopsis*, the salt treatment can induce AtCAPE1 production and even trigger the AtCAPE1 transportation from root to shoot (FIG. 10c). The salt treatment also can enhance the anti-pathogen activity in *Arabidopsis* (FIG. 11), which may due to the CAPE1 production and transportation can be induced by salt stress. This result shows that the movement of CAPE peptides for regulating systemic immune responses.

2.5 the Importance of Conserved Cleavage Motif

To confirm the importance of conserved cleavage motif, we then generated transgenic lines, named CAPE1oxCNAD, where eYFP was fused with PROAtCAPE1 but with a mutation (Y160A) in the CNYx motif. We then examined expression of the mutated PROAtCAPE1-eYFP. Only a single band with a MW of 45.76 kDa was detected in all three independent transgenic lines (FIG. 12). These results suggested that the identified AtCAPE1 was derived from its precursor, PROAtCAPE1, through cleavage at the conserved CNYx motif (SEQ ID NO: 55), and that an aromatic amino residue, tyrosine, is important for the process. We also used the conserved CNYx motif (SEQ ID NO: 55) for designing protease inhibitor to prevent process in tomato. The result showed that the defense gene expression was decreased after the treatment of CNYDPV to tomato plants (FIG. 13).

3. Discussion

In this study, quantitative peptidomics analysis revealed three peptides, including systemin, that were not significantly expressed in the unwounded plant but were expressed at high levels after wounding plus MeJA treatment. This peptide is a signaling molecule for the systemic activation of the anti-herbivore response (Pearce et al., 1991). Systemin is the upstream component of the anti-herbivore signaling cascade and systemic signal transmission is mediated by jasmonic acid (JA) (Li et al., 2003; Stratmann, 2003). We show here the concentration change of endogenous systemin, a well-known wound-induced peptide, before and after the induction of wounding plus MeJA treatment. The detection of systemin also proved that the platform proposed in this study is able to detect defense signaling peptides. The second peptide found to be up-regulated upon treatment was derived from the chloroplast photosystem II subunit X. This peptide may be associated with the induction of reactive oxygen species (ROS) in chloroplasts. The third peptide (designated as CAPE1) was derived from pathogenesis-related protein 1b (PR-1b), a protein of unclear function.

The $H_2O_2$ and defense gene responses induced by CAPE1 indicated that this peptide regulates plant defense responses. $H_2O_2$ is a ROS involved in several defense responses during wounding, insect attacks and pathogen infections (Doke et al., 1996; Lamb and Dixon, 1997; Orozco-Cardenas and Ryan, 1999). CAPE1 was shown to be a DAMP elicitor in this study as it was induced by wounding and activated defense responses. Although several peptides in tomato are proposed to be DAMPs, the evidence for a peptide DAMP is mainly based on the consideration of the precursor gene induced by the damage or the bioactivity of synthesized putative peptides (Pearce et al., 1991; Huffaker et al., 2006; A. P. Trivilin, 2014). Microarray and qRT-PCR analysis showed that CAPE1 can induce defense genes to produce immune responses against herbivores and pathogens. Both JA and SA hormones can be induced by CAPE1, which explains why anti-herbivore and anti-pathogen genes were induced by the peptide treatment. The JA and SA biosynthesis pathways are known to be antagonistic (Robert-Seilaniantz et al., 2011; Thaler et al., 2012) but they may also function synergistically in the SA-JA-ethylene backbone of the plant immune signaling network, thereby redirecting defense output (Verhage et al., 2010). In comparison with the activation of anti-herbivore and anti-pathogen responses by systemin and flg22, respectively, CAPE1 showed a mild anti-herbivore response but activated a comparable anti-pathogen response. The mild anti-herbivore response induced by CAPE1 can be explained by a lower induction level of PI genes and JA hormones than that seen with systemin treatment. CAPE1 significantly induced several pathogen-related marker genes, including PR-2, PR-7, Chi2; 1 and the precursor of CAPE1 (PR-1b). Unlike flg22, which induces WRKY53 (Xiao et al., 2007), the CAPE1 triggered immunity did not induce the PTI responsive gene WRKY53 but induced PR-1b. This implies that flg22 and CAPE1 respectively act as an elicitor for PAMP/MAMP and DAMP and thereby regulate different mechanisms in the anti-pathogen response. In addition, ERF5, a GCC box (AGCCGCC) binding protein, was induced by CAPE1. We suggest that ERF5 is a mediator of CAPE1 defense responses because of the GCC box, a cis-acting element found in the promoter of many jasmonic acid (JA)/ethylene (ET)-inducible and PR genes. ERF5 was also demonstrated to positively regulate SA signaling and plant immunities against the bacterial pathogen Pst DC3000 and improve plant resistance to pathogens by activating several PR genes (Moffat et al., 2012; Son et al., 2012). In tomato, the overexpression of ERF5 was observed to induce PR genes and conferred tolerance to Ralstonia solanacearum (Li et al., 2011). This study suggested an alternative approach to enhance plant resistance through ERF5, which can be regulated by a low concentration of peptide without the use of transgenes. Furthermore, Adi3, encoding a component of the effector-triggered immunity (ETI) response, which negatively regulates programmed cell death (PCD) (Devarenne et al., 2006), was induced after CAPE1 treatment. Adi3 is a cell death suppressor (CDS) and its localization is dictated by a nuclear localization signal found in the Adi3 T-loop extension, which is phosphorylated for kinase activation (Ek-Ramos et al., 2010b). The deactivation of Adi3 CDS function is initiated by the interaction of Pto only when Pto interacts with the Pst effector protein AvrPto. This deactivation of CDS activity can lead to HR, which functions to limit pathogen spread. The HR through deactivation of Adi3 function was demonstrated to be compensated for by overexpression of Adi3 (Devarenne et al., 2006; Ek-Ramos et al., 2010a). In this study, CAPE1 was found to activate a "defense-no-death" phenotype to enhance plant resistance against the bacterial pathogen Pst DC3000 without induction of the HR (Yu et al., 1998). This phenotype could be explained by the elevated level of transcription of anti-pathogen and cell death suppressor genes as well as the level of SA. It also suggests that systemically induced immune responses can be activated by CAPE1, since SA and JA are essential hormones for the induction of SAR and induced systemic resistance (ISR), respectively (Pieterse et al., 2009). Plant insects and pathogens are responsible for substantial crop losses worldwide every year, and amid increasing environmental concerns, the use of agrochemicals to defeat the biological stress is more and more restricted. CAPE1 may potentially be used to activate resistance against biological threats in tomato. Furthermore, the highly conserved sequence of CAPE1 and its proprotein suggests that CAPE1 may also exist and be biologically active in other species. This study demonstrated the role of PR-1b in tomato defense signaling, and also demonstrated that the putative CAPE peptides with a PxGNxxxxxPY- motif (SEQ ID NO: 1) derived from Arabidopsis induces resistance against Pst DC3000 in Arabidopsis. Otherwise, the salt treatment can induce the AtCAPE1 production and transportation from root to shoot. This result indicates that the role of CAPE peptides for systemic immune regulation in diverse plant species. The conserved cleavage motif CNYx (SEQ ID NO: 55) was also identified as an important sequence for the plant immunity by regulating the process. Although At-PR1 is considered to be a common marker gene for the anti-pathogen response, its function was unclear previously. This study highlights the biological role of PR1 and CAP proteins in systemic defense signaling.

REFERENCES

A. P. Trivilin, S.H.a.M.G.M. (2014). Components of different signalling pathways regulated by a new orthologue of AtPROPEP1 in tomato following infection by pathogens. Plant Pathology.

Aebersold, R., and Mann, M. (2003). Mass spectrometry-based proteomics. Nature 422, 198-207.

Boller, T. (2005). Peptide signalling in plant development and self/non-self perception. Curr Opin Cell Biol 17, 116-122.

Boller, T., and Felix, G. (2009a). A renaissance of elicitors: perception of microbe-associated molecular patterns and danger signals by pattern-recognition receptors. Annual review of plant biology 60, 379-406. Boller, T., and Felix, G. (2009b). A Renaissance of Elicitors: Perception of Microbe-Associated Molecular Patterns and Danger Signals by Pattern-Recognition Receptors. Annu Rev Plant Biol 60, 379-406.

Butenko, M. A., Vie, A. K., Brembu, T., Aalen, R. B., and Bones, A. M. (2009). Plant peptides in signalling: looking for new partners. Trends in plant science 14, 255-263.

Campos, M. L., Kang, J. H., and Howe, G. A. (2014). Jasmonate-Triggered Plant Immunity. Journal of chemical ecology.

Chang, W. H., Lee, C. Y., Lin, C. Y., Chen, W. Y., Chen, M. C., Tzou, W. S., and Chen, Y. R. (2013). UniQua: A Universal Signal Processor for MS-Based Qualitative and Quantitative Proteomics Applications. Anal Chem 85, 890-897.

Chassot, C., Buchala, A., Schoonbeek, H. J., Metraux, J. P., and Lamotte, O. (2008). Wounding of Arabidopsis leaves causes a powerful but transient protection against Botrytis infection. The Plant journal: for cell and molecular biology 55, 555-567.

Che, F. Y., Lim, J., Pan, H., Biswas, R., and Fricker, L. D. (2005). Quantitative neuropeptidomics of microwave-irradiated mouse brain and pituitary. Molecular & cellular proteomics: MCP 4, 1391-1405.

Chen, C. J., Chen, W. Y., Tseng, M. C., and Chen, Y. R. (2012). Tunnel Frit: A Nonmetallic In-Capillary Frit for Nanoflow Ultra High-Performance Liquid Chromatography-Mass Spectrometry Applications. Anal Chem 84, 297-303.

Cheong, Y. H., Chang, H. S., Gupta, R., Wang, X., Zhu, T., and Luan, S. (2002). Transcriptional profiling reveals novel interactions between wounding, pathogen, abiotic stress, and hormonal responses in Arabidopsis. Plant Physiol 129, 661-677.

Conesa, A., Gotz, S., Garcia-Gomez, J. M., Terol, J., Talon, M., and Robles, M. (2005). Blast2GO: a universal tool for annotation, visualization and analysis in functional genomics research. Bioinformatics 21, 3674-3676.

Devarenne, T. P., Ekengren, S. K., Pedley, K. F., and Martin, G. B. (2006). Adi3 is a Pdk1-interacting AGC kinase that negatively regulates plant cell death. Embo J 25, 255-265.

Ding, Y., Choi, H., and Nesvizhskii, A. I. (2008). Adaptive discriminant function analysis and reranking of MS/MS database search results for improved peptide identification in shotgun proteomics. Journal of proteome research 7, 4878-4889.

Doke, N., Miura, Y., Sanchez, L. M., Park, H. J., Noritake, T., Yoshioka, H., and Kawakita, K. (1996). The oxidative burst protects plants against pathogen attack: mechanism and role as an emergency signal for plant bio-defence—a review. Gene 179, 45-51.

Du, Z., Zhou, X., Ling, Y., Zhang, Z., and Su, Z. (2010). agriGO: a GO analysis toolkit for the agricultural community. Nucleic acids research 38, W64-70.

Ek-Ramos, M. J., Avila, J., Cheng, C., Martin, G. B., and Devarenne, T. P. (2010a). The T-loop Extension of the Tomato Protein Kinase AvrPto-dependent Pto-interacting Protein 3 (Adi3) Directs Nuclear Localization for Suppression of Plant Cell Death. Journal of Biological Chemistry 285, 17584-17594.

Ek-Ramos, M. J., Avila, J., Cheng, C., Martin, G. B., and Devarenne, T. P. (2010b). The T-loop extension of the tomato protein kinase AvrPto-dependent Pto-interacting protein 3 (Adi3) directs nuclear localization for suppression of plant cell death. The Journal of biological chemistry 285, 17584-17594.

Elias, J. E., and Gygi, S. P. (2007). Target-decoy search strategy for increased confidence in large-scale protein identifications by mass spectrometry. Nature methods 4, 207-214.

Farrokhi, N., Whitelegge, J. P., and Brusslan, J. A. (2008a). Plant peptides and peptidomics. Plant Biotechnol J 6, 105-134.

Farrokhi, N., Whitelegge, J. P., and Brusslan, J. A. (2008b). Plant peptides and peptidomics. Plant Biotechnology Journal 6, 105-134.

Fei, Z., Joung, J. G., Tang, X., Zheng, Y., Huang, M., Lee, J. M., McQuinn, R., Tieman, D. M., Alba, R., Klee, H. J., and Giovannoni, J. J. (2011). Tomato Functional Genomics Database: a comprehensive resource and analysis package for tomato functional genomics. Nucleic acids research 39, D1156-1163.

Francia, D., Demaria, D., Calderini, O., Ferraris, L., Valentino, D., Arcioni, S., Tamietti, G., and Cardinale, F. (2007). Wounding induces resistance to pathogens with different lifestyles in tomato: role of ethylene in cross-protection. Plant, cell & environment 30, 1357-1365.

Fricker, L. D., Lim, J., Pan, H., and Che, F. Y. (2006). Peptidomics: identification and quantification of endogenous peptides in neuroendocrine tissues. Mass spectrometry reviews 25, 327-344.

Gibbs, G. M., Roelants, K., and O'Bryan, M. K. (2008). The CAP superfamily: cysteine-rich secretory proteins, antigen 5, and pathogenesis-related 1 proteins—roles in reproduction, cancer, and immune defense. Endocrine reviews 29, 865-897.

Hayashi, F., Smith, K. D., Ozinsky, A., Hawn, T. R., Yi, E. C., Goodlett, D. R., Eng, J. K., Akira, S., Underhill, D. M., and Aderem, A. (2001). The innate immune response to bacterial flagellin is mediated by Toll-like receptor 5. Nature 410, 1099-1103.

Heath, M. C. (2000). Hypersensitive response-related death. Plant Mol Biol 44, 321-334.

Howe, G. A., Lightner, J., Browse, J., and Ryan, C. A. (1996). An octadecanoid pathway mutant (JL5) of tomato is compromised in signaling for defense against insect attack. Plant Cell 8, 2067-2077.

Huffaker, A., Pearce, G., and Ryan, C. A. (2006). An endogenous peptide signal in *Arabidopsis* activates components of the innate immune response. Proceedings of the National Academy of Sciences of the United States of America 103, 10098-10103.

Initiative, T.A.G. (2000). Analysis of the genome sequence of the flowering plant *Arabidopsis thaliana*. Nature 408, 796-815.

Kapp, E. A., Schutz, F., Connolly, L. M., Chakel, J. A., Meza, J. E., Miller, C. A., Fenyo, D., Eng, J. K., Adkins, J. N., Omenn, G. S., and Simpson, R. J. (2005). An evaluation, comparison, and accurate benchmarking of several publicly available MS/MS search algorithms: sensitivity and specificity analysis. Proteomics 5, 3475-3490.

Lamb, C., and Dixon, R. A. (1997). The oxidative burst in plant disease resistance. Annu Rev Plant Phys 48, 251-275.

Li, C., Liu, G., Xu, C., Lee, G. I., Bauer, P., Ling, H. Q., Ganal, M. W., and Howe, G. A. (2003). The tomato suppressor of prosystemin-mediated responses2 gene encodes a fatty acid desaturase required for the biosynthesis of jasmonic acid and the production of a systemic wound signal for defense gene expression. Plant Cell 15, 1646-1661.

Li, C. W., Su, R. C., Cheng, C. P., Sanjaya, You, S. J., Hsieh, T. H., Chao, T. C., and Chan, M. T. (2011). Tomato RAV transcription factor is a pivotal modulator involved in the AP2/EREBP-mediated defense pathway. Plant Physiol 156, 213-227.

Malinovsky, F. G., Fangel, J. U., and Willats, W. G. (2014). The role of the cell wall in plant immunity. Frontiers in plant science 5, 178.

Mallick, P., and Kuster, B. (2010). Proteomics: a pragmatic perspective. Nature biotechnology 28, 695-709.

Moffat, C. S., Ingle, R. A., Wathugala, D. L., Saunders, N. J., Knight, H., and Knight, M. R. (2012). ERF5 and ERF6 play redundant roles as positive regulators of JA/Et-mediated defense against *Botrytis cinerea* in *Arabidopsis*. PloS one 7, e35995.

Murphy, E., Smith, S., and De Smet, I. (2012). Small signaling peptides in *Arabidopsis* development: how cells communicate over a short distance. Plant Cell 24, 3198-3217.

Narvaez-Vasquez, J., Orozco-Cardenas, M. L., and Ryan, C. A. (2007). Systemic wound signaling in tomato leaves is cooperatively regulated by systemin and hydroxyproline-rich glycopeptide signals. Plant Mol Biol 65, 711-718.

Orozco-Cardenas, M., and Ryan, C. A. (1999). Hydrogen peroxide is generated systemically in plant leaves by wounding and systemin via the octadecanoid pathway. Proceedings of the National Academy of Sciences of the United States of America 96, 6553-6557.

Orozco-Cardenas, M. L., Narvaez-Vasquez, J., and Ryan, C. A. (2001). Hydrogen peroxide acts as a second messenger for the induction of defense genes in tomato plants in response to wounding, systemin, and methyl jasmonate. Plant Cell 13, 179-191.

Pan, X., Welti, R., and Wang, X. (2010). Quantitative analysis of major plant hormones in crude plant extracts by high-performance liquid chromatography-mass spectrometry. Nature protocols 5, 986-992.

Pearce, G., Strydom, D., Johnson, S., and Ryan, C. A. (1991). A Polypeptide from Tomato Leaves Induces Wound-Inducible Proteinase Inhibitor Proteins. Science 253, 895-897.

Pearce, G., Moura, D. S., Stratmann, J., and Ryan, C. A. (2001a). Production of multiple plant hormones from a single polyprotein precursor. Nature 411, 817-820.

Pearce, G., Moura, D. S., Stratmann, J., and Ryan, C. A., Jr. (2001b). RALF, a 5-kDa ubiquitous polypeptide in plants, arrests root growth and development. Proceedings of the National Academy of Sciences of the United States of America 98, 12843-12847.

Pedrioli, P. G. (2010). Trans-proteomic pipeline: a pipeline for proteomic analysis. Methods in molecular biology 604, 213-238.

Pedrioli, P. G., Eng, J. K., Hubley, R., Vogelzang, M., Deutsch, E. W., Raught, B., Pratt, B., Nilsson, E., Angeletti, R. H., Apweiler, R., Cheung, K., Costello, C. E., Hermjakob, H., Huang, S., Julian, R. K., Kapp, E., McComb, M. E., Oliver, S. G., Omenn, G., Paton, N. W., Simpson, R., Smith, R., Taylor, C. F., Zhu, W., and Aebersold, R. (2004). A common open representation of mass spectrometry data and its application to proteomics research. Nature biotechnology 22, 1459-1466.

Pieterse, C. M., Leon-Reyes, A., Van der Ent, S., and Van Wees, S. C. (2009). Networking by small-molecule hormones in plant immunity. Nature chemical biology 5, 308-316.

Robert-Seilaniantz, A., Grant, M., and Jones, J. D. G. (2011). Hormone Crosstalk in Plant Disease and Defense: More Than Just JASMONATE-SALICYLATE Antagonism. Annu Rev Phytopathol 49, 317-343.

Rosli, H. G., Zheng, Y., Pombo, M. A., Zhong, S., Bombarely, A., Fei, Z., Collmer, A., and Martin, G. B. (2013). Transcriptomics-based screen for genes induced by flagellin and repressed by pathogen effectors identifies a cell wall-associated kinase involved in plant immunity. Genome biology 14, R139.

Ryan, C. A., Pearce, G., Scheer, J., and Moura, D. S. (2002). Polypeptide hormones. Plant Cell 14 Suppl, S251-264.

Sasaki, K., Satomi, Y., Takao, T., and Minamino, N. (2009). Snapshot peptidomics of the regulated secretory pathway. Molecular & cellular proteomics: MCP 8, 1638-1647.

Schaller, A., Bergey, D. R., and Ryan, C. A. (1995). Induction of wound response genes in tomato leaves by bestatin, an inhibitor of aminopeptidases. Plant Cell 7, 1893-1898.

Scheer, J. M., and Ryan, C. A. (1999). A 160-kD systemin receptor on the surface of Lycopersicon peruvianum suspension-cultured cells. Plant Cell 11, 1525-1535.

Shiu, S. H., and Bleecker, A. B. (2003). Expansion of the receptor-like kinase/Pelle gene family and receptor-like proteins in Arabidopsis. Plant Physiol 132, 530-543.

Son, G. H., Wan, J., Kim, H. J., Nguyen, X. C., Chung, W. S., Hong, J. C., and Stacey, G. (2012). Ethylene-responsive element-binding factor 5, ERF5, is involved in chitin-induced innate immunity response. Molecular plant-microbe interactions: MPMI 25, 48-60.

Stratmann, J. W. (2003). Long distance run in the wound response—jasmonic acid is pulling ahead. Trends in plant science 8, 247-250.

Svensson, M., Skold, K., Svenningsson, P., and Andren, P. E. (2003). Peptidomics-based discovery of novel neuropeptides. Journal of proteome research 2, 213-219.

Tamura, K., Peterson, D., Peterson, N., Stecher, G., Nei, M., and Kumar, S. (2011). MEGA5: Molecular Evolutionary Genetics Analysis Using Maximum Likelihood, Evolutionary Distance, and Maximum Parsimony Methods. Mol Biol Evol 28, 2731-2739.

Thaler, J. S., Humphrey, P. T., and Whiteman, N. K. (2012). Evolution of jasmonate and salicylate signal crosstalk. Trends in plant science 17, 260-270.

Tinoco, A. D., and Saghatelian, A. (2011). Investigating endogenous peptides and peptidases using peptidomics. Biochemistry 50, 7447-7461.

Verhage, A., van Wees, S. C., and Pieterse, C. M. (2010). Plant immunity: it's the hormones talking, but what do they say? Plant Physiol 154, 536-540.

Xiao, F. M., He, P., Abramovitch, R. B., Dawson, J. E., Nicholson, L. K., Sheen, J., and Martin, G. B. (2007). The N-terminal region of Pseudomonas type III effector AvrPtoB elicits Pto-dependent immunity and has two distinct virulence determinants. Plant Journal 52, 595-614.

Yamaguchi, Y., and Huffaker, A. (2011). Endogenous peptide elicitors in higher plants. Curr Opin Plant Biol 14, 351-357.

Yu, I. C., Parker, J., and Bent, A. F. (1998). Gene-for-gene disease resistance without the hypersensitive response in Arabidopsis dnd1 mutant. Proceedings of the National Academy of Sciences of the United States of America 95, 7819-7824.

Zhou, A., Webb, G., Zhu, X., and Steiner, D. F. (1999). Proteolytic processing in the secretory pathway. The Journal of biological chemistry 274, 20745-20748.

Zimmerli, L., Jakab, G., Metraux, J. P., and Mauch-Mani, B. (2000). Potentiation of pathogen-specific defense mechanisms in Arabidopsis by beta-aminobutyric acid. Proceedings of the National Academy of Sciences of the United States of America 97, 12920-12925.

What is claimed is:

1. A method for inducing systemic immune responses in a plant comprising applying to said plant a plant defense signaling polypeptide comprising a motif of SEQ ID NO: 1 or SEQ ID NO: 28, or a composition comprising the polypeptide, wherein the polypeptide has up to 100 amino acids in length.

2. The method of claim 1, wherein the polypeptide has up to 50 amino acids in length.

3. The method of claim 1, wherein the polypeptide is selected from the group consisting of SEQ ID NOs: 2-27 and SEQ ID NOs: 29-54.

4. The method of claim 1, wherein the systemic immune responses include production of hydrogen peroxide ($H_2O_2$), generation of a plant hormone and/or expression of an anti-herbivore or anti-pathogen protein.

5. The method of claim 1, where the polypeptide or the composition is applied to a surface of the plant.

6. The method of claim 1, where the polypeptide is present in the composition at a concentration of 50 nM or more.

7. The method of claim 1, wherein the polypeptide or the composition is applied to the plant in an amount effective to induce the systemic immune responses within 2 hours and last for more than 24 hours after the polypeptide or the composition is sprayed to the plant.

8. The method of claim 1, further comprising treating the plant with salt.

9. The method of claim 1, wherein the polypeptide has up to 30 amino acids in length.

10. The method of claim 1, wherein the polypeptide has up to 15 amino acids in length.

11. The method of claim 1, wherein the polypeptide consists of SEQ ID NO: 1 or SEQ ID NO: 28.

12. The method of claim 4, wherein the plant hormone is selected from the group consisting of jasmonate (JA), JA conjugated with amino acid isoleucine (JA-Ile), and salicylic acid (SA).

13. The method of claim 5, wherein the surface of the plant is leaves of the plant.

* * * * *